(12) United States Patent
Hiscock et al.

(10) Patent No.: US 11,701,333 B2
(45) Date of Patent: Jul. 18, 2023

(54) ANTIBACTERIAL COMPOUNDS

(71) Applicant: KENT INNOVATION & ENTERPRISE, Canterbury (GB)

(72) Inventors: Jennifer Hiscock, Canterbury (GB); Daniel Mulvihill, Canterbury (GB); Gary Robinson, Canterbury (GB)

(73) Assignee: KENT INNOVATION & ENTERPRISE, Canterbury (GB)

( * ) Notice: Subject to any disclaimer, the term of this patent is extended or adjusted under 35 U.S.C. 154(b) by 0 days.

(21) Appl. No.: 16/632,194

(22) PCT Filed: Jul. 18, 2018

(86) PCT No.: PCT/EP2018/069568
§ 371 (c)(1),
(2) Date: Jan. 17, 2020

(87) PCT Pub. No.: WO2019/016293
PCT Pub. Date: Jan. 24, 2019

(65) Prior Publication Data
US 2021/0128501 A1 May 6, 2021

(30) Foreign Application Priority Data
Jul. 18, 2017 (GB) ..................................... 1711555

(51) Int. Cl.
| | | |
|---|---|---|
| *A61K 31/17* | (2006.01) | |
| *A61P 31/04* | (2006.01) | |
| *A01N 47/30* | (2006.01) | |
| *A01N 47/36* | (2006.01) | |
| *A01N 47/44* | (2006.01) | |
| *A01N 57/22* | (2006.01) | |
| *A61K 31/155* | (2006.01) | |
| *A61K 31/428* | (2006.01) | |
| *A61K 31/513* | (2006.01) | |
| *A61K 31/662* | (2006.01) | |
| *A61K 45/06* | (2006.01) | |

(52) U.S. Cl.
CPC .............. *A61K 31/17* (2013.01); *A01N 47/30* (2013.01); *A01N 47/36* (2013.01); *A01N 47/44* (2013.01); *A01N 57/22* (2013.01); *A61K 31/155* (2013.01); *A61K 31/428* (2013.01); *A61K 31/513* (2013.01); *A61K 31/662* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | | | |
|---|---|---|---|---|
| 7,173,102 | B2 * | 2/2007 | DeGrado | A01N 47/30 |
| | | | | 428/152 |
| 9,446,090 | B2 * | 9/2016 | Bevilacqua | A61K 45/06 |
| 10,912,299 | B2 * | 2/2021 | Herdt | A01N 25/02 |

OTHER PUBLICATIONS

Hiscock et al., "In situ modification of nanostructure configuration through the manipulation of hydrogen bonded amphiphile self-association", Apr. 7, 2016, Soft Matter, 12(18), pp. 4221-4228. (DOI: 10.1039/c6sm00529b) (Year: 2016).*
White et al., "Towards quantifying the role of hydrogen bonding within amphiphile self-association and resultant aggregate formation", 2017, Chem. Sci., 8(11), pp. 7620-7630. (DOI: 10.1039/c7sc03888g) (Year: 2017).*
White et al., "Controllable hydrogen bonded self-association for the formation of multifunctional antimicrobial materials", 2020, J. Mater. Chem. B, 8(21), pp. 4694-4700. (DOI: 10.1039/d0tb00875c) (Year: 2020).*
English Abstract of Japanese Patent Publication No. JPS57175189 (1982).

(Continued)

*Primary Examiner* — My-Chau T. Tran
(74) *Attorney, Agent, or Firm* — Jeffrey N. Townes; Cozen O'Connor

(57) ABSTRACT

The present invention relates to certain compounds of formula (I) wherein—Ar is (Ar1) or (Ar2) and to their uses as antibacterial agents. The invention further relates to methods of treatment of bacterial infection with such compounds, optionally in combination with other antimicrobials and to compositions and pharmaceutical formulations containing such compounds. The invention additionally relates to coatings containing such compounds and to items having such coatings.

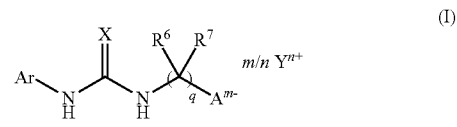

(I)

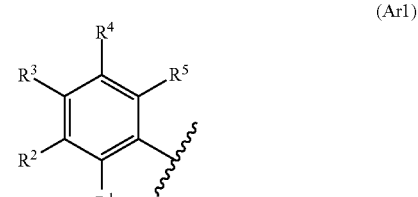

(Ar1)

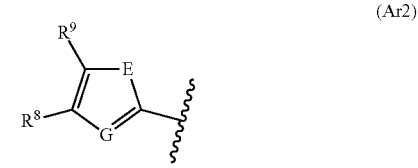

(Ar2)

18 Claims, 3 Drawing Sheets

(56) References Cited

OTHER PUBLICATIONS

O'Brien et al., "New Mannich reaction of pyrimidines," Journal of Heterocyclic Chemistry 3: 115-116 (1966) (abstract).

Tait et al., "Bacteria detection based on the evolution of enzyme-generated volatile organic compounds: Determination of Listeria monocytogenes in milk samples," Analytica Chimica Acta 848: 80-87 (2014) (abstract).

Vorslova et al., "Application of the Solvatic Model for Prediction of Retention in RP-LC for Multi-Step Gradient Profiles," Chromatographia 78: 899-908 (2015) (abstract).

White et al., "Towards the Prediction of Global Solution State Properties for Hydrogen Bonded, Self-Associating Amphiphiles," Chemistry—A European Journal 24: 7761-7773 (2018).

Tsutsumi et al., "Improvement of antileprous drugs. III. Inhibitory effect of some drugs on the growth of leprosy bacilli in the footpads of mice," Repura 39: 33-47 (1970) (English abstract).

Muller et al., "Carboxylic acid replacement structure-activity relationships in sousan type sweeteners. A sweet taste antagonist. 1," Journal of Medicinal Chemistry 35: 1747-1751 (1992) (abstract).

Garrigues et al., "Salts of N-alkysulfonated ureas and thioureas," Synthesis 10: 810-813 (1988) (abstract).

Athiel et al., "Degradation of iprodione by a soil Arthrobacter-like strain," Applied and Environmental Microbiology 61: 3216-3220 (1995) (abstract).

Glasser et al., "3-Substituted 2-thiohydrouracils. Synthesis and antitubercular and antineoplastic activities," Journal of Medicinal Chemistry 9: 351-353 (1966) (abstract).

Petersen et al., "A new group of sweet substances," Chemische Berichte 81: 31-38 (1948) (abstract).

Scozzafava et al., "Antimycobacterial Activity of 3,4-dichlorophenyl-ureas, N,N-diphenyl-ureas and Related Derivatives," Journal of Enzyme Inhibition 16: 425-432 (2001).

Fu et al., "Is *Mycobacterium tuberculosis* a closer relative to Gram-positive or Gram-negative bacterial pathogens?," Tuberculosis 82: 85-90 (2002).

Morris et al., "Ancestral antibiotic resistance in *Mycobaterium tuberculosis*," PNAS 102: 12200-12205 (2005).

\* cited by examiner

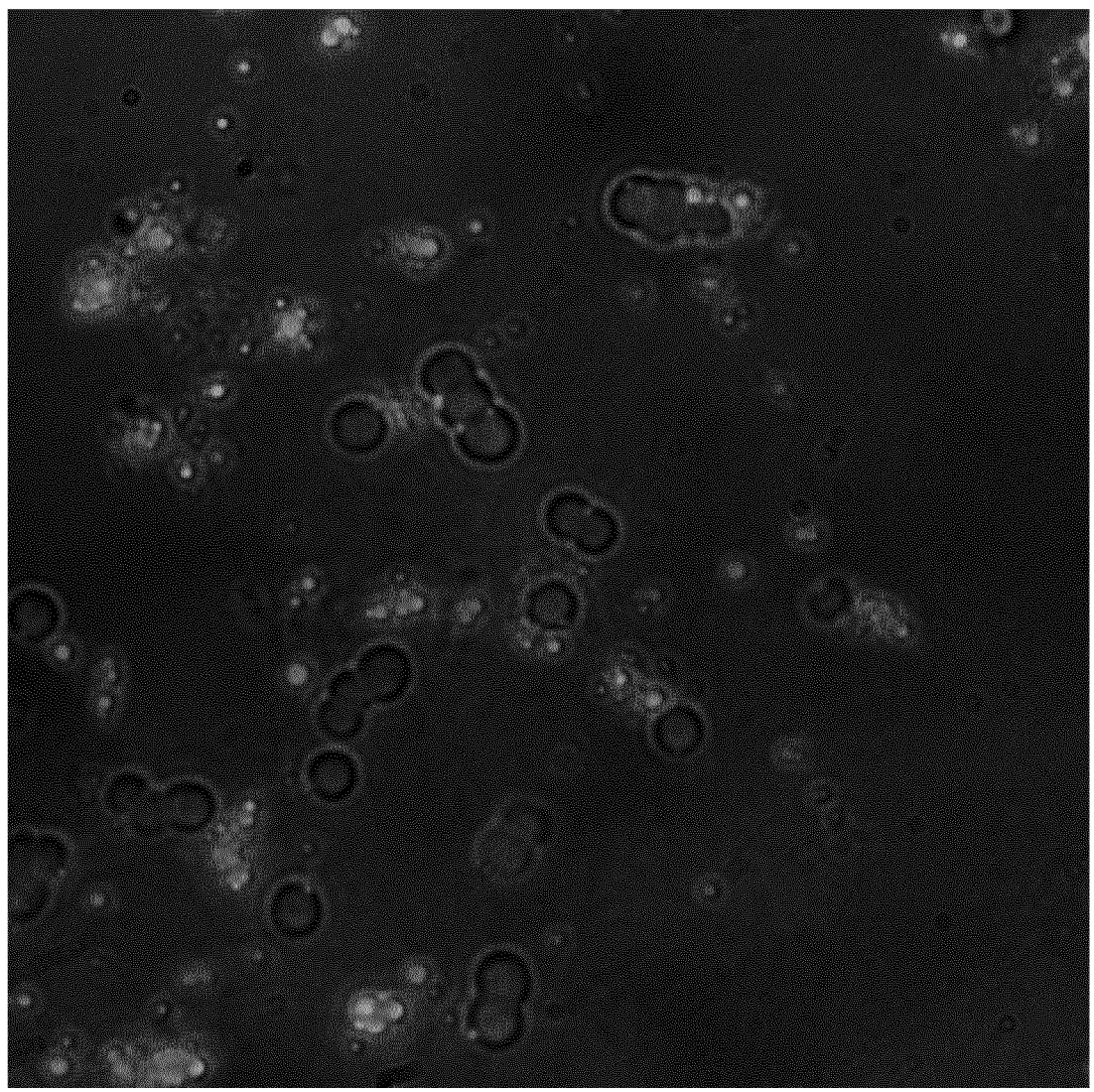
Figure 1: Fluorescence microscopy image of Staphylococcus aureus upon the addition of compound 53 (shown in green).

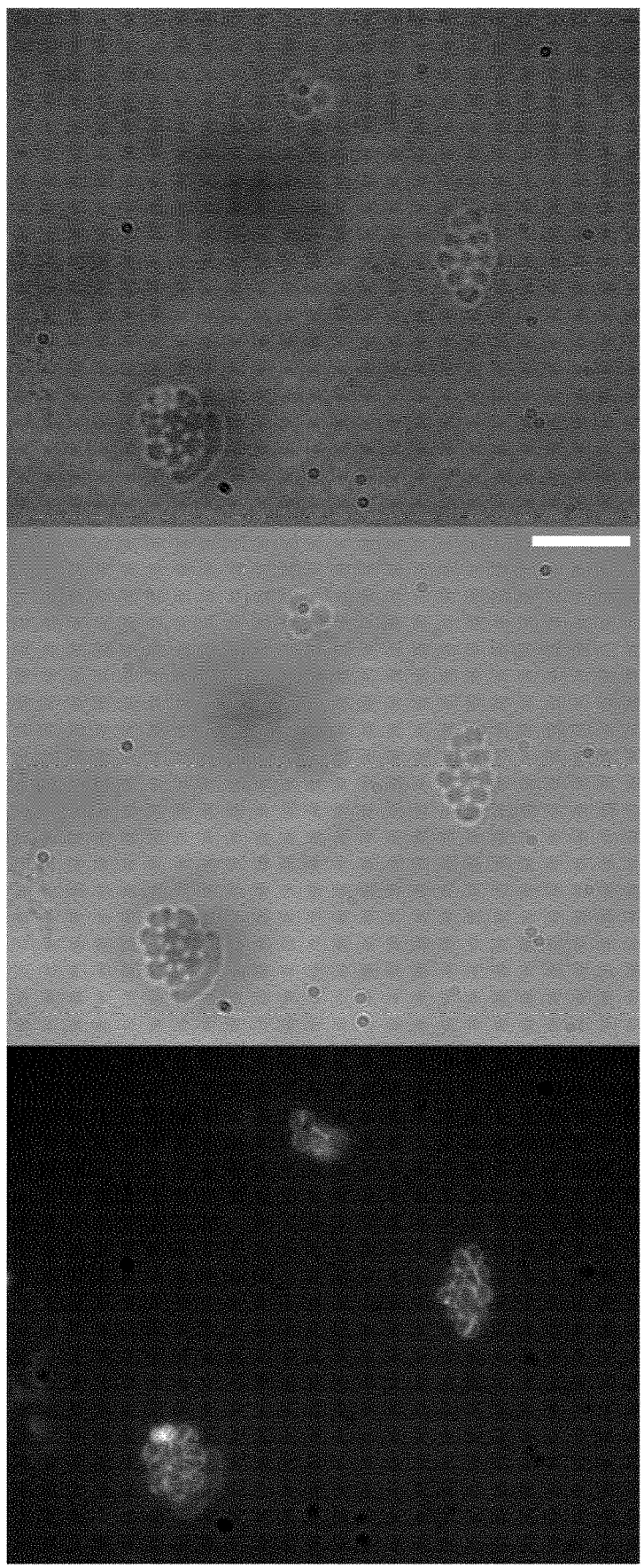
Figure 2: Microscopy images of both Staphylococcus aureus and E. coli in the presence of an increased concentration of the same compound (compound 53).

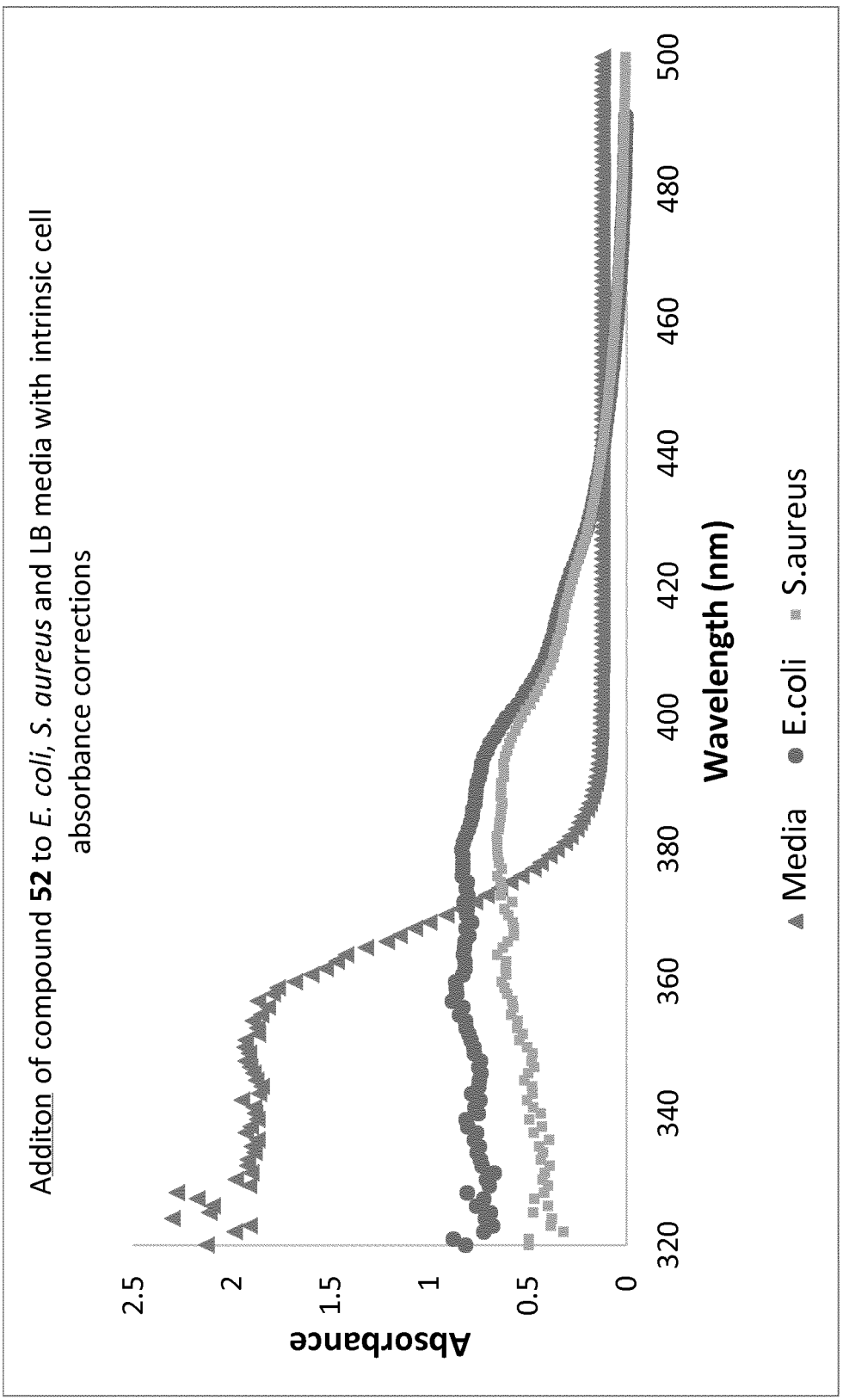
Figure 3: Addition of compound 52 to E. coli, S. aureus and LB media with intrinsic cell absorbance corrections.

ANTIBACTERIAL COMPOUNDS

CROSS-REFERENCE TO RELATED APPLICATIONS

This application is a 371 National-Stage application of International PCT Application No. PCT/US2018/069568, filed Jul. 18, 2018, and claims priority to GB Patent Application No. 1711555.1, filed Jul. 18, 2017, both of which are incorporated herein by reference in their entirety.

FIELD OF THE INVENTION

The present invention relates to compounds with antibacterial properties and their use as antibacterial agents, as antibiotic medicaments, and/or in antibacterial coatings. The invention furthermore generally relates to processes for the preparation of such compounds.

BACKGROUND TO THE INVENTION

The rise in antibacterial resistance is one of the most pressing health concerns of the $21^{st}$ century. New classes of antibacterial agents are needed in order to overcome the emergence of antibiotic-resistant bacteria, and in particular new classes of compounds that may target bacteria via mechanisms which are unlikely to cause the easy acquisition of antibiotic resistance. It would give a significant advantage to provide an effective class of antimicrobial agents, and in particular antibiotic medicaments. Gram-negative bacteria tend to be more difficult to treat and therefore there is a particular need to develop drugs which are effective these (Brown, E. D.; Wright, G. D. Nature 2016, 259, 336-343), although new antibiotics and antimicrobial compounds of all types and for use against any potentially pathogenic microbes provide a very important contribution.

Antimicrobial agents play a large role in many different applications. These include, for example, household applications such as antibacterial sprays and wipes, antimicrobial pesticide or other industrial products as well as human and animal pharmaceutical products such as antibiotics, antifungals, antivirals and antiparasitics. Antimicrobials may, of course, have more than one beneficial use.

The present inventors have focused on developing new antibacterial agents with the aim of addressing some of the key problems in the field. More than 20 new classes of antibiotics were discovered between 1940 and 1962, but only two new classes have reached the market since then (Coates, A. R. M. et al., British Journal of Pharmacology 2011, 163, 184-194). It would therefore be highly desirable in the first instance to provide a new class of compounds with a fundamentally different core structure to the known classes of drugs on the market. It would also be beneficial to develop a synthetic method which enables the facile synthesis of these compounds to enable the easy modification of the structure to investigate antimicrobial properties. A simple synthetic method would also have obvious advantages in terms of preparation time, cost and potentially yield. Furthermore, it would be beneficial if the new class of compounds can show antimicrobial activity against gram-positive and/or against the more difficult-to-treat gram-negative bacteria. Finally, in order to pre-empt antibacterial resistance, it would be beneficial if the compounds were able to target bacteria via mechanisms which are different from those for which known resistance mechanisms exist and still more beneficial if such mechanisms were unlikely to cause the easy acquisition of new antibiotic resistance.

The present inventors have developed a new class of antibacterial compounds which address some or all of the above issues. They have surprisingly established that certain compounds with an aromatic unit and an oxygen-containing anionic group show bactericidal activity against Gram +ve (e.g. S. aureus, Bacillus megaterium) and bacteristatic activity against Gram −ve isolates (e.g. E. coli). The compounds disclosed herein have been designed, synthesised and altered in a step-wise systematic manner to facilitate the elucidation of compound structure—anti-microbial activity relationships, and are made following a method which enables a previously multi-step process to be simplified to a one-pot reaction.

SUMMARY OF THE INVENTION

In a first aspect, the invention provides the use of a compound of formula (I):

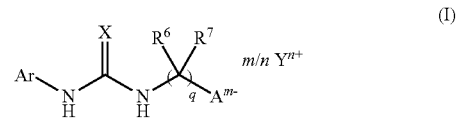

wherein
Ar is

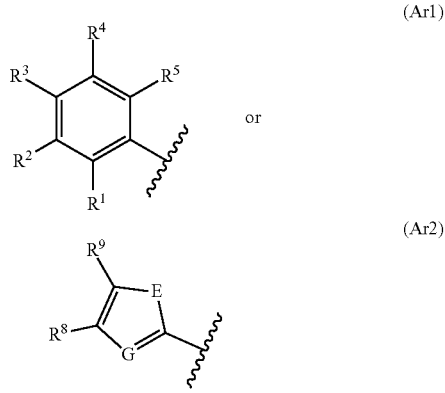

X is O, S, NH;
A is such that $A^{m-}$ is an oxygen-containing anionic group;
Y is such that $Y^{n+}$ is an inorganic or organic cation or proton ($H^+$);
G is N or CH
E is S, O or NH
$R^6$ and $R^7$ are independently selected for each value of q from hydrogen or a straight-chain, branched chain or cyclic or polycyclic $C_1$ to $C_{10}$ hydrocarbyl group, preferably hydrogen;
$R^1$-$R^5$, $R^8$ and $R^9$ are selected from hydrogen, —$CF_3$, —$CCl_3$, —$NHR^{10}$, —$NR_2^{10}$, —$OR^{16}$, —OH, —NHC(O)$R^{10}$, —OCOR$^{10}$, —COH, —COR$^{10}$, COOH, COOR$^{10}$, CONH$_2$, —CN, —SO$_3$H NO$_2$, —OMe, —NH$_2$, halogen (e.g. F, Cl, Br, I), CONHR$^{10}$, —C(O)NH(CH$_2$)SO$_3$—, a straight-chain, branched chain or cyclic or polycyclic $C_1$ to $C_{10}$ hydrocarbyl group, a cyclic or polycylic group comprising 1 or more heteroatoms selected from O, N and S and optionally further substituted with a straight-chain or branched chain C1-C8 hydrocarbyl group, or a nucleobase-containing group, such as:

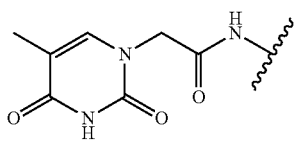 [SMILES: *NC(=O)Cn1cc(C)c(=O)[nH]c1=O]

and/or
at least one of the pairs of groups $R^1/R^2$, $R^2/R^3$, $R^3/R^4$ and $R^4/R^5$ is such that the pair(s) form a cyclic or polycyclic moiety, optionally comprising one or more heterotatoms, fused to the benzene ring in Ar1, or the pair $R^8/R^9$ forms a cyclic or polycyclic moiety fused to the ring substituted with G and E in Ar2 wherein the cyclic or polycyclic moiety is optionally substituted with a straight-chain or branched chain C1-C8 hydrocarbyl group, $R^{10}$ is a straight-chain, branched chain or cyclic or polycyclic $C_1$ to $C_{10}$ hydrocarbyl group;

q is an integer from 1-10, preferably 1-6, more preferably 1-4; and m and n are each independently an integer from 1-3, preferably 1; as an antibacterial agent.

In a particular embodiment, the invention provides the use as defined above wherein $A^{m-}$ is selected from -SO₃, —PO₃H⁻, PO₃²⁻, —COO⁻.

In a further particular embodiment, the invention provides the use as defined above, wherein G is N and E is S.

In a further particular embodiment, the invention provides the use as defined above, wherein
if Ar=Ar1, at least one of $R^1$-$R^5$ is selected from CF₃, NO₂, OMe, NMe₂, NH₂, F or from the following groups:

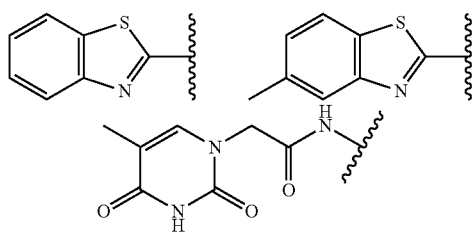

and/or at least one of the pairs of groups R1/R2, R2/R3, R3/R4 and R4/R5 form a cyclic or polycylic moiety, optionally comprising one or more heterotatoms; or
if Ar=Ar2, R1 and R2 form a benzene ring fused to the ring substituted with G and E, wherein the benzene ring is optionally substituted with a straight-chain or branched chain C1-C8 hydrocarbyl group such as methyl.

In a further aspect, the invention provides the use of a compound of formula (II):

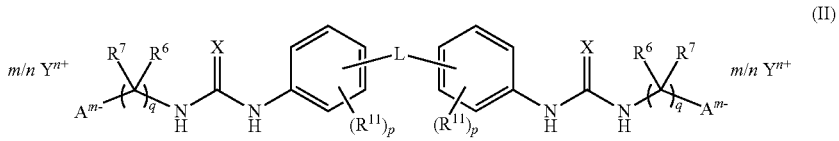

(II)

wherein X, $R^6$, $R^7$, A, Y, m, n and q are as defined in any of claims 1-5;

L is a linker group selected from a straight-chain, branched chain or cyclic or polycyclic C1 to C10 hydrocarbyl group optionally containing one or more ether linkages;

$R^{11}$ is selected from —CF₃, —CCl₃, —NHR¹⁰, —NR₂¹⁰, —OR¹⁰, —OH, —NHC(O)R¹⁰, —OCOR¹⁰, —COH, —COR¹⁰, COOH, COOR¹⁰, CONH₂, —CN, —SO₃H, NO₂, —OMe, —NH₂, halogen (e.g. F, Cl, Br, I), a straight-chain, branched chain or cyclic or polycyclic $C_1$ to $C_{10}$ hydrocarbyl group, wherein $R^{10}$ is as defined for formula (I)

p is an integer from 0 to 4;

as an antibacterial agent.

In a further particular embodiment, the invention provides a use as defined above, wherein said use is as an antibacterial agent against Gram-positive bacteria, such as staphylococci.

In a further particular embodiment, the invention provides a use as defined above, wherein said use is as an antibacterial agent against Gram-negative bacteria, such as Enterobacteriaceae.

In a further aspect, the invention provides a method of reducing the number or preventing the multiplication of live bacteria on a surface comprising a step of applying to the surface a solution of a compound of formula (I) or formula (II).

In a further aspect, the invention provides the compound of formula (I) or (II) for use as an antibiotic medicament.

In a particular embodiment, the invention provides the compound for use as defined above, for use as an antibiotic medicament against Gram-positive bacteria, such as staphylococci, and/or Gram-negative bacteria, such as Enterobacteriaceae.

In a further aspect, the invention provides a method of treatment of a bacterial infection comprising administering to an animal, preferably a mammal, e.g. human, an effective amount of at least one compound of formula (I) or (II).

In a further aspect, the invention provides the use of a compound of formula (I) or (II) in the manufacture of a medicament for the treatment of a bacterial infection.

In a further aspect, the invention provides a pharmaceutical composition comprising the compound of formula (I) or (II), further comprising additives and/or excipients suitable for parenteral, oral or topical administration.

In a further aspect, the invention provides a dispensing device comprising:
a chamber containing a solution of a compound of formula (I) or (II); and
a dispensing mechanism, e.g. a spray pump.

In a further aspect, the invention provides an antimicrobial coating composition comprising
a binder
at least one compound of formula (I) or (II).

In a further aspect, the invention provides an object coated with an antimicrobial coating composition as defined above.

In a further aspect, the invention provides a process for increasing the antimicrobial properties of an object comprising coating at least a part of said object with an anti-antimicrobial coating composition as defined above.

In a further aspect, the invention provides a compound of formula (I) or (II), wherein the compound is not one of the following:

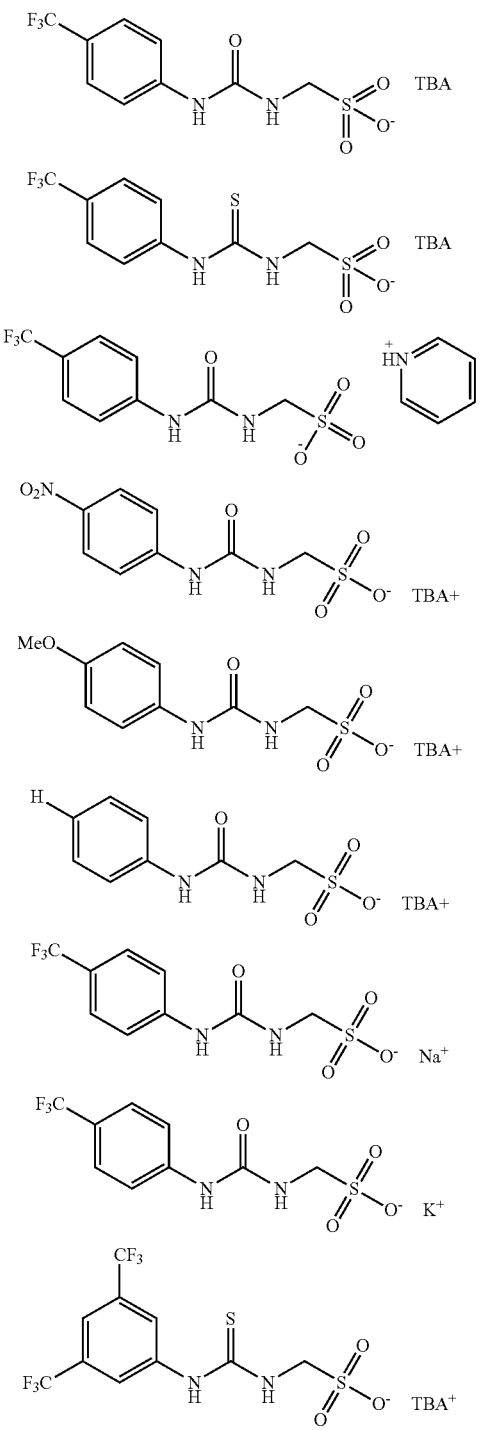

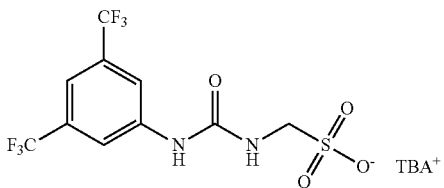

In a further aspect, the invention provides a process for the preparation of a compound of formula I, comprising a step of reacting a compound of formula

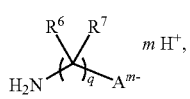

with a compound of formula

preferably wherein Ar is Ar1.

In a further aspect, the invention provides a process for the preparation of a compound of formula I, comprising a step of reacting a compound of formula

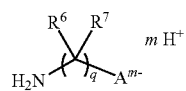

with a compound of formula

in the presence of a coupling agent; preferably wherein Ar is Ar2.

The features of the aspects and/or embodiments indicated herein are usable individually and in combination in all aspects and embodiments of the invention where technically viable, unless otherwise indicated.

DETAILED DESCRIPTION OF THE INVENTION

The present invention relates to the use of the following compounds of formula (I) as antibacterial agents:

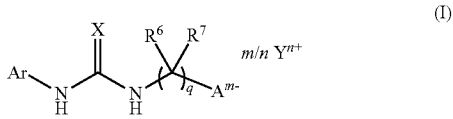

wherein Ar is

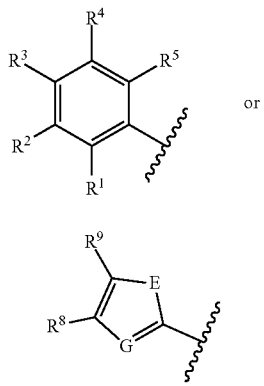

In the above formula (I), X is preferably selected from O, S, Se, NH, NR, wherein R is a straight-chain, branched chain or cyclic or polycyclic $C_1$ to $C_{10}$ hydrocarbyl group, more preferably X is selected from O, S, and NH.

In the above formula (I), A is such that $A^{m-}$ is an oxygen-containing anionic group. The group $A^{m-}$ is preferably a hydrogen-donating anionic component. By oxygen-containing anionic group is meant an oxygen-containing group with the negative charge(s) on oxygen. For example ether-type fragments of formula such as —($CH_2$)—O—$CH_2$ are not considered here to be oxygen-containing anionic groups. The oxygen-containing anionic group is a key feature of the compounds of the invention and appears to be important for antimicrobial activity. Any oxygen-containing anionic group can in theory be used, but in a typical embodiment A is such that $A^{m-}$ is selected from $-SO_3^-$, $-OSO_3^-$, $-OSO_2^-$, $-SO_2^-$, $-OPO_3H^-$, $-OPO_3^{2-}$, $-PO_3H^-$, $-PO_3^{2-}$, $-PR'O_2^-$, $-OPR'O_2^-$, $-COO^-$, $-OCOO^-$, wherein R' is a straight-chain, branched chain or cyclic or polycyclic $C_1$ to $C_{10}$ hydrocarbyl group. In a particular embodiment, A is such that $A^{m-}$ is selected from $-SO_3^-$, $-PO_3H^-$, $-PO_3^{2-}$, or $-COO^-$.

In the above formula (I), Y is such that $Y^{n+}$ is an inorganic or organic cation or proton ($H^+$). In the case of pharmaceutical applications (e.g. as antibiotics), it is envisaged that any standard pharmaceutically-acceptable cation may be used. Typically, the inorganic or organic cation will be selected from pyridinium, tetraalkylammonium, alkali metal ions (e.g. $Li^+$, $Na^+$, $K^+$), alkaline earth metal ions (e.g. $Mg^{2+}$ or $Ca^{2+}$); preferably pyridinium, THA ([$N^nHex_4$]$^+$), TPeA ([$N^nPed$]$^+$), TBA ([$N^nBu_4$]$^+$), TPA ([$N^nPr_4$]$^+$), TEA ([$N^nEt_4$]$^+$), TMA ([$N^nMe_4$]$^+$), $Na^+$, $K^+$. In the case of the oxygen-containing anionic group $A^{m-}$ having m as an integer of 2 or more, the cationic component of the compound may consist of one cation $Y^{n+}$ with n=m, or 2 or more cations with n=1. For the case in which $Y^{n+}$ is proton ($H^+$), the compound may be considered a neutral compound with, for example, neutral $-SO_3H$, $-PO_3H_2$, or $-COOH$ groups. Preferably, if $Y^{n+}$ is a proton, the $A^{m-}$-$mH^+$ unit is not an alcohol. Furthermore, if $Y^{n+}$ is a proton, preferably the pKa (in $H_2O$ at 25° C.) of the $A^{m-}$-$mH^+$ unit is 10 or less In further embodiments, if $Y^{n+}$ is a proton, the pKa (in $H_2O$ at 25° C.) of the $A^{m-}$-$mH^+$ unit may be 9 or less, such as 8 or less.

The integers m and n are each independently an integer from 1-3, preferably 1 or 2, preferably 1.

In the above formula (I), $R^6$ and $R^7$ are independently selected for each value of q from hydrogen or a straight-chain, branched chain or cyclic or polycyclic $C_1$ to $C_{10}$ hydrocarbyl group, preferably hydrogen. The compound of formula(I) may therefore be substituted in these positions with common alkyl or aryl functional groups; for example, R6 and R7 may be independently selected for each value of q from methyl, ethyl, n/iso-propyl, or phenyl. In a particularly preferred embodiment, both $R^6$ and $R^7$ are hydrogen (for all values of q).

In the above formula (I), q is an integer from 1-10, preferably 1-6, more preferably 1-4.

If Ar=Ar1 in the above formula (I), $R^1$-$R^5$ are typically independently selected from hydrogen, $-CF_3$, $-CCl_3$, $-NHR^{10}$, $-NR_2^{10}$, $-OR^{10}$, $-OH$, $-NHC(O)R^{10}$, $-OCOR^{10}$, $-COH$, $-COR^{10}$, COOH, $COOR^{10}$, $CONH_2$, $-CN$, $-SO_3H$ $NO_2$, $-OMe$, $-NH_2$, $NMe_2$, halogen (e.g. F, Cl, Br, I), $CONHR^{10}$, $-C(O)NH(CH_2)SO_3-$, a straight-chain, branched chain or cyclic or polycyclic $C_1$ to $C_{10}$ hydrocarbyl group (such as methyl, ethyl, propyl (n- or iso-), butyl (sec-, n-, tert- or iso-), or phenyl), a cyclic or polycylic group comprising 1 or more heteroatoms selected from O, N and S and optionally further substituted with a straight-chain or branched chain C1-C8 hydrocarbyl group, or a nucleobase-containing group, such as:

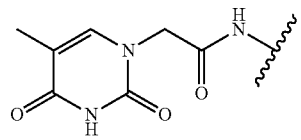 [SMILES: *NC(=O)Cn1cc(C)c(=O)[nH]c1=O]

and/or at least one of the pairs of groups $R^1/R^2$, $R^2/R^3$, $R^3/R^4$ and $R^4/R^5$ is such that the pair(s) form a cyclic or polycyclic moiety, optionally comprising one or more heterotatoms, fused to the benzene ring in Ar1, in particular a thiazole, benzene or naphthalene unit fused to the benzene ring depicted in Ar1; and $R^{10}$ is a straight-chain, branched chain or cyclic or polycyclic $C_1$ to $C_{10}$ hydrocarbyl group, such as methyl, ethyl, propyl (n- or iso-), butyl (sec-, n-, tert- or iso-), or phenyl.

By nucleobase-containing group is meant any group containing Adenine, Guanine, Cytosine, Thymine or Uracil groups or derivatives. Such nucleobases or nucleobase derivatives may be modified with simple groups which enable linkage to the Ar1 group. Other analogous structures with hydrogen bond donating/accepting functionalities are also envisaged.

In a typical embodiment, at least one of $R^1$-$R^5$ is selected from hydrogen, —$CF_3$, —$NO_2$, —OMe, —$NH_2$, $NMe_2$, F, or from the groups

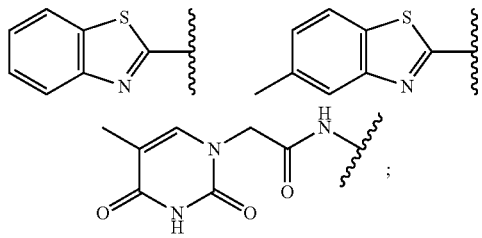

or $R^1$-$R^5$ are such that the Ar1 group is:

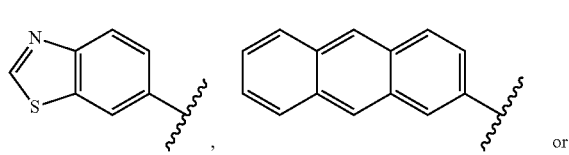 or

-continued

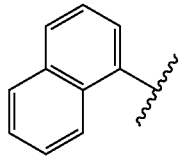

In a particular embodiment, the Ar1 group is substituted at the $R^3$ position, i.e. $R^1$, $R^2$, $R^4$ and $R^5$ are all hydrogen, and $R^3$ is selected from the above groups but is not hydrogen; typically in this case $R^3$ is selected from —$CF_3$, —$NO_2$, —OMe, —$NH_2$, $NMe_2$ and the group

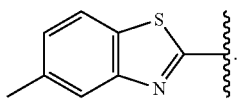

Of these, $R^3$ as —$CF_3$ constitutes a particularly preferred embodiment. In another embodiment, the Ar1 group is substituted at the $R^2$ and $R^4$ positions; in this case, $R^1$, $R^3$ and $R^5$ are H, and $R^2$ and $R^4$ are selected from —$CF_3$, —$NO_2$, —OMe, —$NH_2$ and $NMe_2$, in particular $CF_3$. In another embodiment, all of $R^1$-$R^5$ are the same, typically F. In a further embodiment, the Ar1 group may be substituted at the $R^1$- or $R^5$-position, in particular with the group

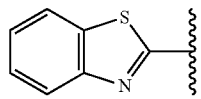 [SMILES: *c1nc2ccccc2s1]

If Ar=Ar2, G is typically N or CH, preferably N, and E is typically S, O or NH, preferably S. Preferably, Ar2 is a thiazole or thiazole derivative. In a particular embodiment, the pair $R^8/R^9$ forms a cyclic or polycylic moiety fused to the ring substituted with G and E, wherein the cyclic or polycyclic moiety is preferably benzene, and is optionally substituted with a straight-chain or branched chain C1-C8 hydrocarbyl group (e.g. straight or branched C1-C8 alkyl group, in particular methyl, ethyl, or a an aryl group, such as phenyl). In a preferred embodiment, if Ar=Ar2, then Ar is selected from:

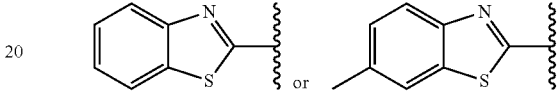 or

In a further embodiment, the invention relates to the use of the following compounds of formula (II) as antibacterial agents:

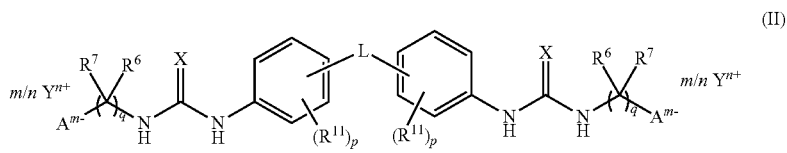

(II)

wherein X, $R^6$, $R^7$, A, Y, m, n and q are as defined in formula (I).

In the above formula (II), L is a linker group selected from a straight-chain, branched chain or cyclic or polycyclic $C_1$ to $C_{10}$ hydrocarbyl group optionally containing one or more ether linkages. In a particular embodiment, the linker L is a C1-C10 linear alkyl chain, such as a C1-C4 linear alkyl chain, preferably —$CH_2$—, or a linear C1-C10 alkyl chain capped on both ends by two ether linkages, preferably a linear C1-C4 alkyl chain capped on both ends by two ether linkages, e.g. —O—$(CH_2)_3$—O—.

In the above formula (II), $R^{11}$ is selected from —$CF_3$, —$CCl_3$, —$NHR^{10}$, —$NR_2^{10}$, —$OR^{10}$, —OH, —NHC(O)$R^{10}$, —$OCOR^{10}$, —COH, —$COR^{10}$, COOH, $COOR^{16}$, $CONH_2$, —CN, —$SO_3H$, $NO_2$, —OMe, —$NH_2$, halogen (e.g. F, Cl, Br, I), a straight-chain, branched chain or cyclic or polycyclic $C_1$ to $C_{10}$ hydrocarbyl group, wherein $R^{10}$ is as defined for formula (I). Preferably, $R^{11}$ is —$CF_3$.

In the above formula (II), p is an integer from 0 to 4, preferably 0 or 1.

Examples of compounds of formula (I) and (II) suitable for use as antibacterial agents according to the present invention are shown in Table 1:

TABLE 1
Example compounds of formula (I) and (II)
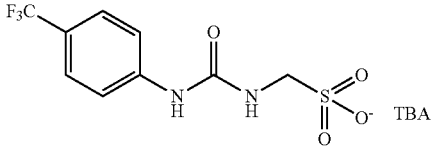 [SMILES: O=C(NCS(=O)(=O)[O-])Nc1ccc(C(F)(F)F)cc1] 1
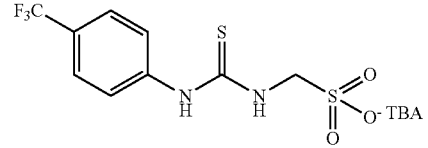 [SMILES: O=S(=O)([O-])CNC(=S)Nc1ccc(C(F)(F)F)cc1] 2
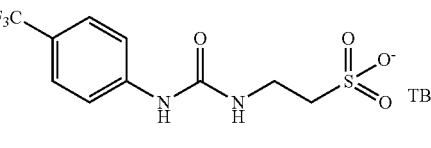 3
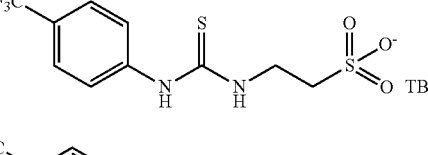 4
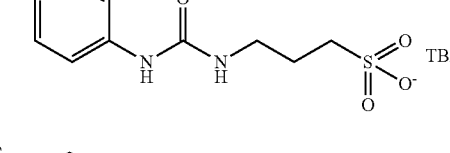 5
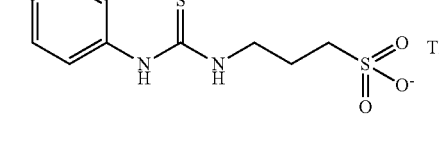 6
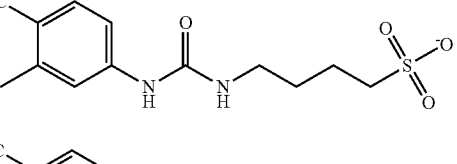 7
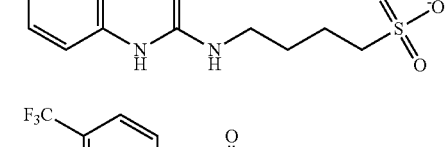 8
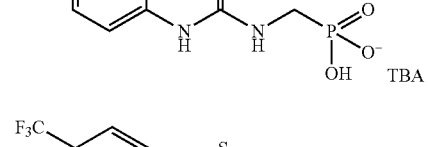 9
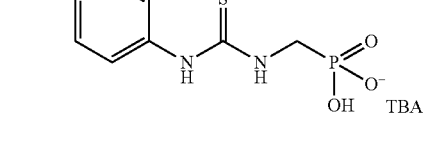 10

TABLE 1-continued
Example compounds of formula (I) and (II)
| Structure | # |
|---|---|
| 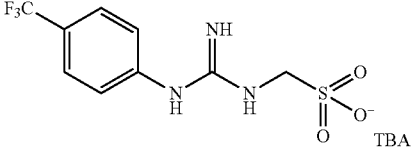 [SMILES: N=C(NCS(=O)(=O)[O-])Nc1ccc(C(F)(F)F)cc1] | 11 |
| 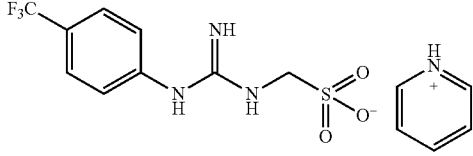 | 12 |
| 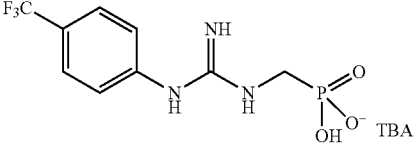 [SMILES: N=C(NCP(=O)([O-])O)Nc1ccc(C(F)(F)F)cc1] | 13 |
| 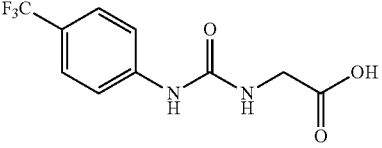 | 18 |
| 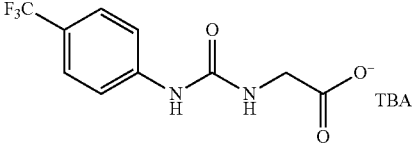 [SMILES: O=C([O-])CNC(=O)Nc1ccc(C(F)(F)F)cc1] | 19 |
| 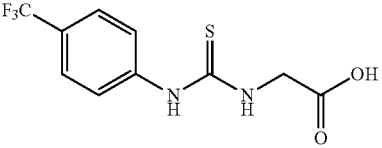 | 21 |
| 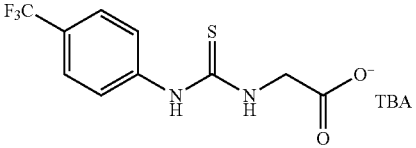 [SMILES: O=C([O-])CNC(=S)Nc1ccc(C(F)(F)F)cc1] | 22 |
| 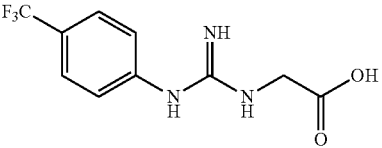 [SMILES: N=C(NCC(=O)O)Nc1ccc(C(F)(F)F)cc1] | 25 |
| 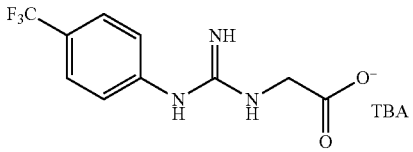 [SMILES: N=C(NCC(=O)[O-])Nc1ccc(C(F)(F)F)cc1] | 26 |

TABLE 1-continued
Example compounds of formula (I) and (II)
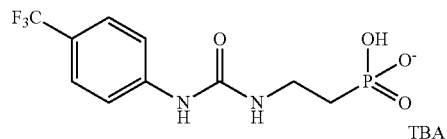 [SMILES: O=C(NCCP(=O)([O-])O)Nc1ccc(C(F)(F)F)cc1] 27
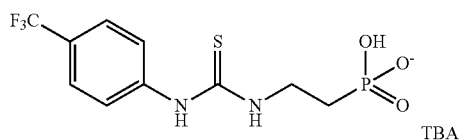 [SMILES: O=P([O-])(O)CCNC(=S)Nc1ccc(C(F)(F)F)cc1] 28
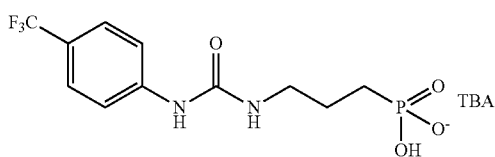 [SMILES: O=C(NCCCP(=O)([O-])O)Nc1ccc(C(F)(F)F)cc1] 29
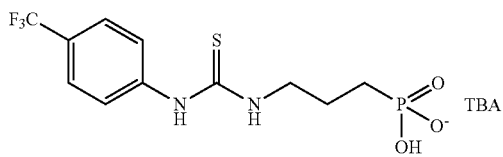 [SMILES: O=P([O-])(O)CCCNC(=S)Nc1ccc(C(F)(F)F)cc1] 30
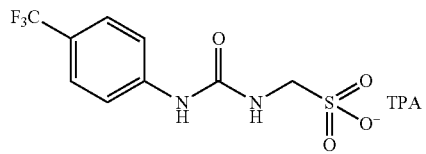 [SMILES: O=C(NCS(=O)(=O)[O-])Nc1ccc(C(F)(F)F)cc1] 31
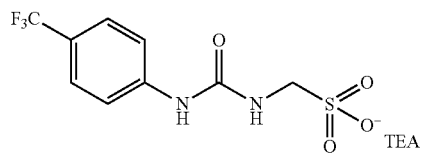 [SMILES: O=C(NCS(=O)(=O)[O-])Nc1ccc(C(F)(F)F)cc1] 32
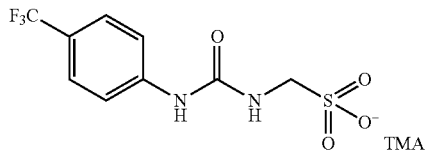 33
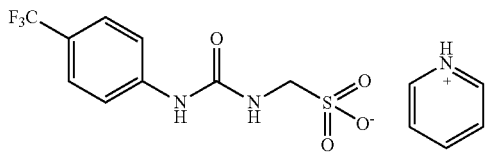 34
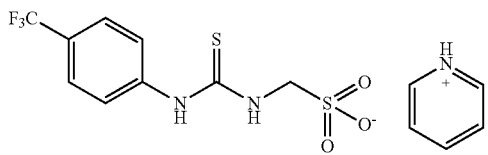 35

TABLE 1-continued

Example compounds of formula (I) and (II)

| Structure | # |
|---|---|
| 4-(CF₃)C₆H₄-NH-C(=O)-NH-CH₂-SO₃⁻ TPA | 36 |
| 4-(CF₃)C₆H₄-NH-C(=O)-NH-CH₂-SO₃⁻ THA | 37 |
| 4-(O₂N)C₆H₄-NH-C(=O)-NH-CH₂-SO₃⁻ TBA⁺ | 38 |
| 4-(MeO)C₆H₄-NH-C(=O)-NH-CH₂-SO₃⁻ TBA⁺ | 39 |
| C₆H₅-NH-C(=O)-NH-CH₂-SO₃⁻ TBA⁺ | 40 |
| 4-(CF₃)C₆H₄-NH-C(=O)-NH-CH₂-SO₃⁻ Na⁺ | 41 |
| 4-(CF₃)C₆H₄-NH-C(=O)-NH-CH₂-SO₃⁻ K⁺ | 42 |
| 3,5-(CF₃)₂C₆H₃-NH-C(=S)-NH-CH₂-SO₃⁻ TBA⁺ | 43 |
| 3,5-(CF₃)₂C₆H₃-NH-C(=O)-NH-CH₂-SO₃⁻ TBA⁺ | 44 |

TABLE 1-continued
Example compounds of formula (I) and (II)
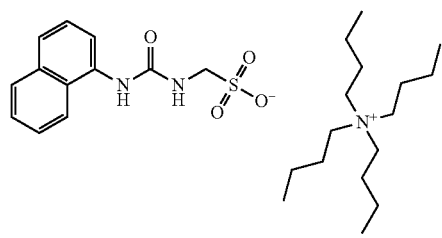 [SMILES: O=C(NCS(=O)(=O)[O-])Nc1cccc2ccccc12 ; CCCC[N+](CCCC)(CCCC)CCCC] 45
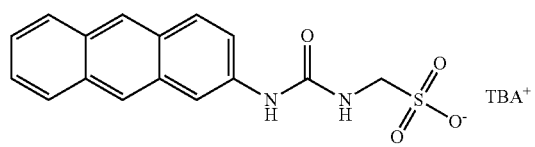 [SMILES: O=C(NCS(=O)(=O)[O-])Nc1ccc2cc3ccccc3cc2c1] 52
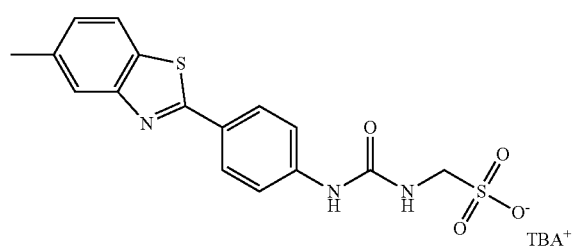 [SMILES: Cc1ccc2sc(-c3ccc(NC(=O)NCS(=O)(=O)[O-])cc3)nc2c1] 53
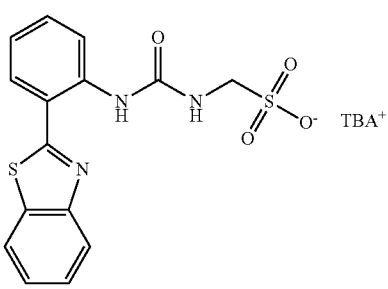 [SMILES: O=C(NCS(=O)(=O)[O-])Nc1ccccc1-c1nc2ccccc2s1] 54
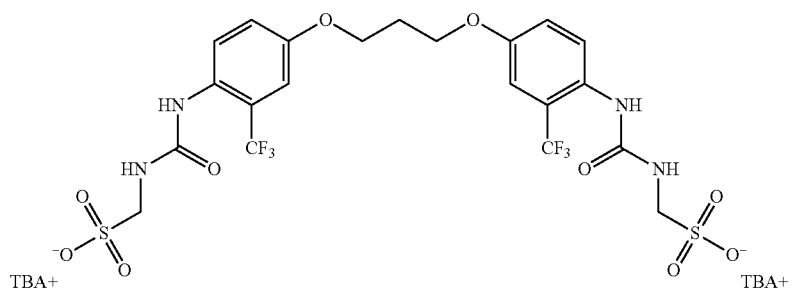 55
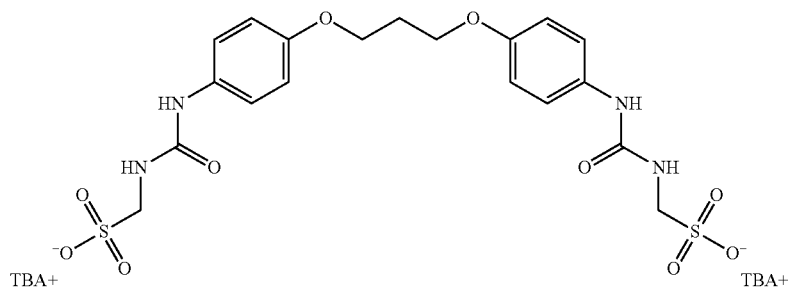 56

TABLE 1-continued

Example compounds of formula (I) and (II)

| Structure | Label | No. |
|---|---|---|
| F₃C-C₆H₄-NH-C(=S)-NH-CH₂-SO₃⁻ | TPeA | 57 |
| F₃C-C₆H₄-NH-C(=S)-NH-CH₂-SO₃⁻ | Na+ | 58 |
| F₃C-C₆H₄-NH-C(=S)-NH-CH₂-SO₃⁻ | K+ | 59 |
| F₃C-C₆H₄-NH-C(=NH)-NH-CH₂-SO₃⁻ | TPeA+ | 60 |
| F₃C-C₆H₄-NH-C(=S)-NH-CH₂-SO₃⁻ | TMA+ | 61 |
| F₃C-C₆H₄-NH-C(=S)-NH-CH₂-SO₃⁻ | TEA+ | 62 |
| F₃C-C₆H₄-NH-C(=S)-NH-CH₂-SO₃⁻ | TPA+ | 63 |
| 5-methyluracil-N-CH₂-C(=O)-NH-C₆H₄-NH-C(=O)-NH-CH₂-SO₃⁻ | TBA+ | 64 |
| C₆F₅-NH-C(=O)-NH-CH₂-SO₃⁻ | TBA | 65 |

TABLE 1-continued
Example compounds of formula (I) and (II)
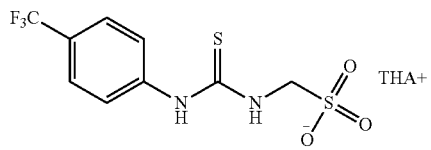 66
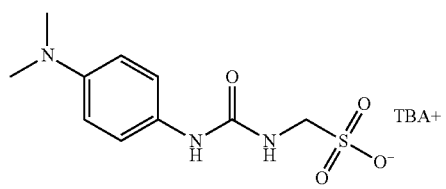 67
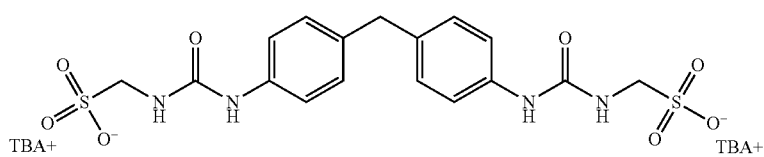 [SMILES: O=C(NCS(=O)(=O)[O-])Nc1ccc(Cc2ccc(NC(=O)NCS(=O)(=O)[O-])cc2)cc1] 68
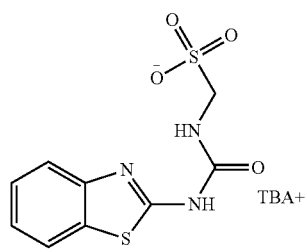 [SMILES: O=C(NCS(=O)(=O)O)Nc1nc2ccccc2s1] 71
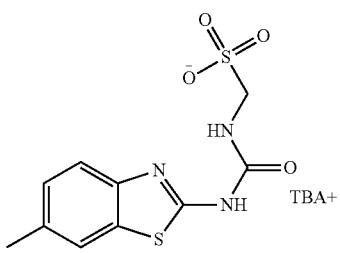 [SMILES: Cc1ccc2nc(NC(=O)NCS(=O)(=O)O)sc2c1] 72
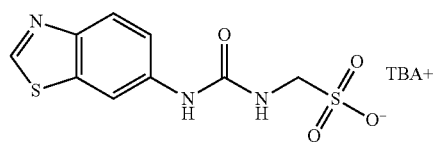 73
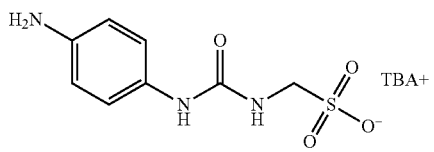 74
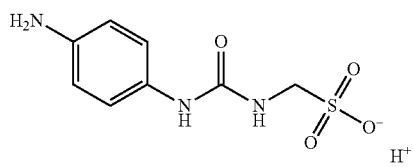 75

The present invention therefore concerns the above compounds and their uses in all aspects of the invention. For example, the present invention relates to the use of the above compounds as antibacterial agents.

In a further embodiment, at least one of the compounds indicated herein in any aspect may be used as an antimicrobial (especially antibacterial) agent alone or in combination with another active agent. In particular, at least one of the compounds of all aspects of the invention may be used in combination with another antibiotic (especially antibacterial) agent. Preferably such other antibiotic agent may be from another category of antibiotic agents, such as beta-lactam antibiotics, macrolide antibiotics, cephalosporin antibiotics, fluoroquinolone antibiotics, sulfonamide antibiotics, tetracycline antibiotics, aminoglycoside antibiotics or any combination thereof. Such other antibiotic may thus be, for example, a beta-lactam antibiotic, a macrolide antibiotic, a cephalosporin antibiotic, a fluoroquinolone antibiotic, a sulfonamide antibiotic, a tetracycline antibiotic, an minoglycoside antibiotic or any combination from one or more of such categories of antibiotics.

Such combination use may be routine use (e.g. in order provide enhanced antibiotic efficacy) or may be for use in treating antibiotic-resistant bacteria/infections or to re-sensitise a bacterial strain which is at least partially resistant to an existing antibiotic agent or category of antibiotic agents. Correspondingly, the combination use may be for avoiding the development and/or increase in antibiotic resistance.

Combination use may be in the form of a single formulation/medicament or by contemporaneous administration (simultaneously or sequentially) of two or more medicaments each containing at least one antibiotic agent, including at least one medicament containing at least one compound as described in any aspect of the present invention.

In corresponding formulations, the compounds of the present invention may be formulated with other antimicrobial (e.g. antibacterial/antibiotic) agent(s) for combination use in vivo or ex vivo. Thus, the invention provides a composition comprising at least one compound as indicated in any aspect of the present invention and at least one other antimicrobial agent, preferably at least one chlorinated antimicrobial agent (such as triclosan and/or triclocarban), especially for ex vivo use. In an alternative aspect, the invention provides a pharmaceutical formulation comprising at least one compound as indicated in any aspect of the present invention and at least one other antibiotic agent (e.g. selected from the group of beta-lactam antibiotics, macrolide antibiotics, cephalosporin antibiotics, fluoroquinolone antibiotics, sulfonamide antibiotics, tetracycline antibiotics, aminoglycoside antibiotics or any combination thereof). Pharmaceutical formulations may optionally include at least one pharmaceutically acceptable carrier or excipient such as water for injection, sterile buffers or saline, cream or ointment bases or etc.

The invention correspondingly provides the use of at least one compound as described in any aspect of the present invention (e.g. a compound of formula (I) or (II)) and at least one other antibiotic agent in the manufacture of a combination medicament for the treatment of bacterial infection. Such combination may be as described above, such as with at least one other antibiotic agent (e.g. selected from the group of beta-lactam antibiotics, macrolide antibiotics, cephalosporin antibiotics, fluoroquinolone antibiotics, sulfonamide antibiotics, tetracycline antibiotics, aminoglycoside antibiotics or any combination thereof). Said bacterial infection may be an infection by at least one (at least partially) antibiotic resistant strain of bacteria. Said treatment may be for treatment of a bacterial infection by at least one known or proposed antibiotic resistant strain of bacteria or for treatment of a bacterial infection while avoiding or reducing the development of antibiotic resistance. Where said treatment is of a bacterial infection by at least one known or proposed antibiotic resistant strain of bacteria, said treatment may be to re-sensitise such a known or proposed resistant strain.

In certain optional embodiments, the compound of formula (I) is not one or more of the following:
- a compound of formula I wherein simultaneously $R^3=CF_3$, X=O, q=3, and $A^{m-}=SO_3$
- a compound of formula I, wherein $R^3$ is MeO.
- a compound of formula I, wherein $R^1$-$R^5$ are all H.
- a compound of formula I, wherein simultaneously $R^3=CF_3$, X=O, q=1, $A^{m-}=SO_3$ and m/n $y^{n+}=K^+$;
- a compound of formula I, wherein R1 or R5 is:

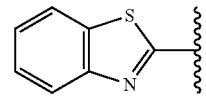 [SMILES: *c1nc2ccccc2s1]

- a compound of formula I, wherein $R^3=CF_3$, X=S, q=1, $A^{m-}=SO_3^-$, and m/n $Y^{n+}=TPA$;

or
- a compound of formula I, wherein $R^1$-$R^5$ are all F.

Each of the above optional exclusions may be applied individually or in any technically viable combination.

To the extent that any of the compounds shown in Table 1 (e.g. compounds 1, 2, 34, 38, 39, 40, 41, 42, 43, 44) may already be known (Hiscock, J. R. et al., Soft Matter, 2016, 12, 4221-4228; Hiscock, J. R. et al., CrystEngComm, 2016, 18, 7021-7028), their use as antimicrobial agents has not previously been reported. Their use in the various other aspects of the invention is therefore new. The invention also relates to the previously unreported compounds per se. In a particular embodiment therefore, the invention relates to compounds of formula (I) or (II) which are not one of the following:

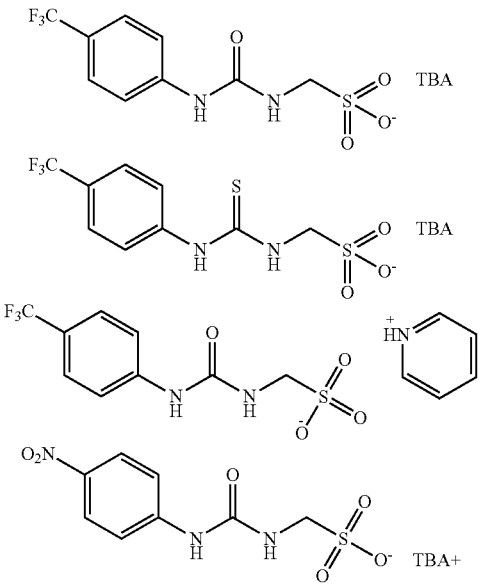

-continued

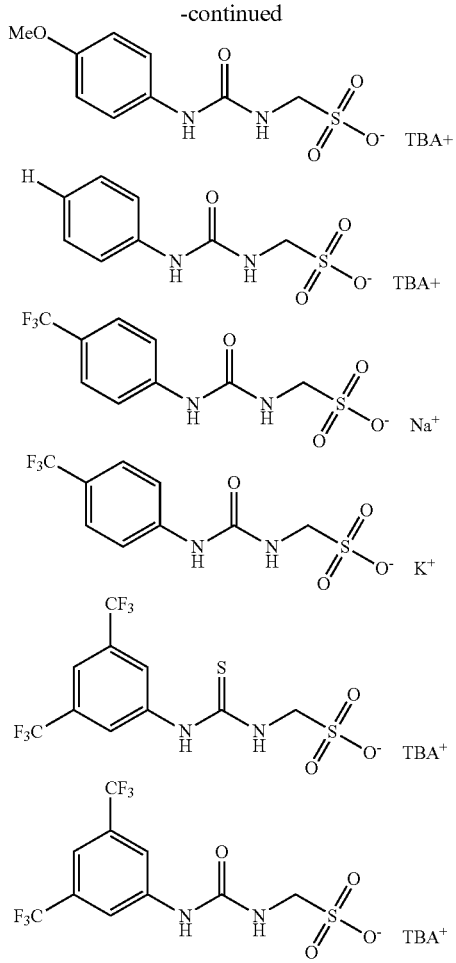

Preparation

The present inventors have developed synthetic methods which enable the one-pot preparation of the compounds of formula I and II. Previous methods, for example those described for the synthesis of compounds 1, 2, 34 and 38-44 in Hiscock, J. R. et al., Soft Matter, 2016, 12, 4221-4228; Hiscock, J. R. et al., CrystEngComm, 2016, 18, 7021-7028, require a multi-step process and/or the use of starting materials such as isocyanates/triphosgene and triphosgene that are undesirable in large scale synthesis. The processes of the present invention not only enable the compounds to be prepared simply and in high yield and high purity, but they are also advantageous in that the structures can be varied with ease in order to tune the structures to affect the antimicrobial properties with a reduction in the proportion of hazardous materials used. In a first typical process, the key bond-forming step for the preparation of compounds of formula I is the reaction between an isocyanate and an amine. In a particular embodiment therefore, the invention provides a process for the preparation of a compound of formula I, comprising a step of reacting a compound of formula

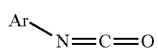

with a compound of formula

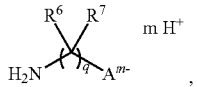

preferably wherein Ar is Ar1 (particularly as described in the various aspects and preferred embodiments herein).

In some cases the isocyanate reagent is commercially available, but if not it can be prepared from the reaction of an amine with triphosgene or other suitable reagent. We note that the reaction of an amine with triphosgene may lead to a carbamoyl chloride (—NH(CO)Cl). However, given the instability of this species due to its propensity to lose HCl, the isocyanato mechanism is the more probable.

This first process is evidently only suitable for the preparation of compounds of formula (I) in which X is O. In order to prepare the compounds of formula I in which X is S, the appropriate amine was reacted with the corresponding isocyanate. In order to prepare compounds of formula (I) in which X is NH, the corresponding thiourea was reacted with ammonium hydroxide and 2-Iodoxybenzoic acid. This first process is particularly suitable for the preparation of compounds of formula I which have Ar=Ar1.

In another typical process, the key —HN—(C=X)—NH— group is formed by reaction of two amines and a coupling agent. Any coupling agent which forms an —HN—(C=X)—NH— moiety from two amines would be suitable. A typical suitable coupling agent is carbonyldiimidazole (CDI). In a further embodiment therefore, the invention provides a process for the preparation of a compound of formula I, comprising a step of reacting a compound of formula

with a compound of formula

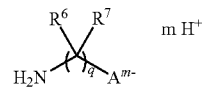

in the presence of a coupling agent. This process is particularly suitable for the preparation of compounds with Ar=Ar2.

Use as an antimicrobial/antibacterial agent

In one aspect, the invention relates to the use of the compounds of formula (I) or (II) as antibacterial agents. The antibacterial agents of the invention may be applied as a solution to a surface by means of a dispensing device. Such a dispensing device may comprise
  a chamber containing a solution of a compound of formula (I) or (II); and
  a dispensing mechanism, e.g. a spray pump such as a manual or electric spray pump.

The solvent for the solution of the compound (I) or (II) may be any suitable solvent used for the application of antibacterial solution to surfaces. In a particular embodiment, the solution may be an aqueous or predominantly aqueous solution, such as an aqueous fluid in which the solvent system comprises a water content of greater than 70 wt %, greater than 80 wt %, greater than 90 wt %, greater than 95 wt %, or greater than 98 wt %.

The fluid may also comprise other common solvents (especially at least partially water soluble solvents) such as alcohols (e.g. ethanol and/or iso-propanol), esters (e.g. ethyl acetate) and/or ketones (e.g. acetone). These solvents may have the added benefit that they inherently possess disinfecting properties, are more volatile than water and/or may enhance solubility of the compounds described herein. For example, a typical solution according to the present invention may comprise up to 10 wt %, up to 20 wt %, up to 30 wt %, up to 40 wt %, or up to 50 wt % of a solvent (e.g. an alcohol), such as ethanol or isopropanol, or of a mixture of two or more alcohols.

In the present invention, a single compound of formula (I) or (II) may be used, or a mixture of two or more different compounds may be used. The compounds of the invention may also be combined with other standard antimicrobial agents, such as benzoalkonium chloride or didecyldimethylammonium chloride, or natural oils such as lavender, citrus, tea tree, or *eucalyptus*. The solution may also comprise a variety of other standard ingredients, such as colourants, perfumes, viscosity modifiers etc.

The invention furthermore relates to a method of reducing the number of live bacteria on a surface, or inhibiting the multiplication of bacteria on a surface, comprising a step of applying to the surface a solution of a compound of formula (I) or (II) as defined herein. It is believed that the compounds of the present invention encapsulate the microorganisms and this encapsulation leads to the antibacterial effect.

It is also within the scope of the invention for the antibacterial to be used as a wipe.

Use as an Antibiotic

In a further aspect of the invention, the compounds of the present invention may be used as an active component in antibiotic medicaments. In a particular aspect the invention provides a pharmaceutical composition comprising the compound of formula (I) or (II), further comprising additives and/or excipients suitable for pharmaceutical use (e.g. for parenteral, oral or topical administration).

In the case of oral administration, the compounds of the invention may be formulated as tablets. Tablets may be plain, film or sugar coated, bisected, embossed, layered, or sustained release. Any film coating preferably comprise a physiologically acceptable water-soluble organic polymer. They can be made in a variety of sizes, shapes and colours.

Excipients which may be present include diluents, binders, disintegrants, lubricants, glidants and in many cases, colorants. The excipients used are classified according to the function they perform. For example, a glidant may be used to improve the flow of powder blend in the hopper and into the tablet die.

Lubricants are typically added to prevent the tableting materials from sticking to punches, minimize friction during tablet compression, and allow for removal of the compressed tablet from the die. Such lubricants are commonly included in the final tablet mix in amounts usually less than 1% by weight. The most commonly used lubricants are magnesium stearate, stearic acid, hydrogenated oil, and sodium stearyl fumarate.

Tablets often contain diluents, such as lactose, which are added to increase the bulk weight of the blend resulting in a practical size for compression. This is often necessary where the dose of the drug is relatively small. Typical diluents include for example dicalcium phosphate, calcium sulphate, lactose, cellulose, kaolin, mannitol, sodium chloride, dry starch and other sugars.

Binders are agents which impart cohesive qualities to the powdered material. Commonly used binders include starch, gelatin, sugars such as sucrose, glucose, dextrose, and lactose, natural and synthetic gums, carboxymethylcellulose, methylcellulose, polyvinylpyrrolidone, ethylcellulose and waxes.

Disintegrants are often included to ensure that the tablet has an acceptable rate of disintegration. Typical disintegrants include starch derivatives, crospovidone, croscaramelose and salts of carboxymethylcellulose. Some binders, such as starch and cellulose, are also excellent disintegrants. Appropriate choices of coating, binder and/or disintegrant may be used to affect the site of release in the GI tract in order to enhance or control absorption of the compounds described herein.

Antioxidants can also be present. Preferred antioxidants include ascorbyl palmitate, butyl hydroxy anisole (BHA), butyl hydroxy toluene (BHT) and citric acid.

Other desirable characteristics of excipients include high compressibility to allow strong tablets to be made at low compression forces, good flow properties that can improve the flow of other excipients in the formula and cohesiveness (to prevent tablet from crumbling during processing, shipping and handling). The skilled man knows the type of excipients appropriate for tablet formulation.

Suppository dosage forms using known pharmaceutical excipients (e.g. "Hard fat" suppository bases or "Hydrophilic" suppository bases) may be used if necessary to avoid excessive "first pass" metabolism by the hepatic system.

In the case of parenteral administration (e.g. transcutaneous or intravenous) the compound is preferably formulated in a sterile aqueous solution, optionally including excipients such as pH and/or tonicity adjusters. Thus the pharmaceutical composition may be an aqueous solution of the compound of the formula (I) or (II) comprising further additives/excipients suitable for parenteral administration.

In a particular embodiment, the invention concerns the compound of formula (I) or (II) for use as an antibiotic medicament and/or for use in the treatment of local or systemic bacterial infection. In a further embodiment, the invention provides a method of treatment of a bacterial infection comprising administering to an animal, preferably a mammal, e.g. human, an effective amount of at least one compound of formula (I) or (II). In a further embodiment, the invention provides the use of a compound of formula (I) or (II) in the manufacture of a medicament for the treatment of a bacterial infection.

Again, a single compound of formula (I) or (II) may be used, or a mixture of two or more different compounds may be used.

Treatment and medical use aspects of the invention will typically be for the treatment of bacterial infection. Such infection may be due to any (especially pathogenic) bacteria but will typically be by gram positive and/or gram negative bacteria.

Examples of gram-positive bacteria which may be treated in the various aspects of the present invention include gram-positive cocci such as *staphylococcus* (e.g. *S. aureus* or *S. saprophyticus*), *streptococcus* (e.g. *S. pyogenes, S. agalactiae, S. pneumonia* or *Viridans* streptococci), or *Enterococcus* (*E. faecalis* or *E. faecium*) or gram-positive bacilli such as *Clostridium* (e.g. *C. botulinum, C. difficile*), *Listeria* (e.g. *L. monocytogenes*), *Bacillus* (e.g. *B. anthracis* or *B. cereus*) or *Corynebacterium* (e.g. *C. diphtheria*).

Examples of gram-negative bacteria which may be treated in the various aspects of the present invention include Proteobacteria such as *Escherichia* (e.g. *E. coli*), *Salmonella* (e.g. *S. enterica* or *S. bongori*), *Vibrio* (e.g. *V. cholerae, V. parahaemolyticus*, or *V. vulnificus*), *Helicobacter* (e.g. *H.*

*pylori*) or *Yersinia* (e.g. *Y. pestis*), gram-negative cocci such as *Neisseria* (e.g. *N. meningitidis* or *N. gonorrhoeae*) or *Moraxella* (e.g. *M. catarrhalis*, or *M. lacunata*), or gram-negative bacilli such as *Legionella* (e.g. *L. pneumophila*) or *Pseudomonas* (e.g. *P. aeruginosa* or *P. oryzihabitans*).

Most suitable bacteria for treatment with the compounds of the present invention in any aspect include *staphylococcus* such as *S. aureus*, *Bacillus* such as *B. megaterium* and/or *Escherichia* such as *E. coli*. *S. aureus* is a most preferred bacterium for treatment and/or control in the various aspects, methods and uses of the present invention.

In a typical embodiment of the invention, the compounds of the present invention are used as antibacterial agents/antibiotic agents against Gram-positive bacteria, such as staphylococci. In a further embodiment, the compounds of the present invention are used as antibacterial agents/antibiotic agents against Gram-negative bacteria, such as Enterobacteriaceae. Such Gram-positive and/or Gram-negative bacteria are envisaged to be suitable targets in all aspects and embodiments of the invention, whether the compounds of the invention are used as antibacterial agents, as pharmaceutical compounds, in coatings, from a dispensing device etc.

Use as an antimicrobial coating The compounds of the present may also be used in antimicrobial coating compositions. In particular, the invention provides an antimicrobial coating composition comprising:

a binder; and at least one compound of formula (I) or (II).

In a particular embodiment, the binder is a polymeric binder, such as a supramolecular or covalently-linked hydrogel. In practice, any binder may be used as long as the compounds of the invention may disperse or dissolve well in them. It is envisaged that the compounds may be added to varnishes, paints, lacquers, and any other types of coating. The invention furthermore provides a process for increasing the antimicrobial properties of an object comprising coating at least a part of said object with an anti-antimicrobial coating composition as defined herein. The invention also provides an object coated with an antimicrobial coating composition as defined herein.

Antibacterial Properties

The ability of each of the compounds of the invention to impact bacterial growth and viability has been tested. This has been undertaken using a novel drop-test method for initial activity screening, as well as using conventional growth curve analysis methodology. This novel class of antimicrobial agent has shown bactericidal activity against Gram +ve (e.g. *S. aureus*, *Bacillus megaterium*) and bacteriostatic activity against Gram −ve isolates (e.g. *E. coli*).

The present inventors have determined $MIC_{50}$ values, in the nM-μM range, for lead compounds, against clinical *S. aureus* isolates (e.g. MRSA) and *E. coli* in both log and stationary phases. The lead compounds do not impact mammalian cell or whole organism viability or development (e.g. HEK & HeLa cells, yeast or nematode worms). Evidence suggests that the compounds do not associate with the membranes of these higher animals.

The lead compounds have been found to retain their antimicrobial properties against clinical *S. aureus* isolates (e.g. MRSA) when impregnated into a soft material ie. they are capable of formulation and diffusion.

Examples

Synthesis

The synthetic methods for some of the compounds are given below. Any of the example syntheses below can be used to prepare any compound of formula through some modest alteration.

Compound 1: 1-lsocyanato-4-(trifluoromethyl)benzene (0.32 g, 1.82 mM) was added to a stirring solution of aminomethanesulfonic acid (0.21 g, 1.82 mM) in anhydrous pyridine (10 mL) under an inert atmosphere. The mixture was heated to 60° C. overnight. The pyridinium salt was then removed by filtration. Yield: 82% (0.56 g, 1.49 mM). The pyridinium salt (0.20 g, 0.53 mM) was dissolved in a 1M solution of tetrabutylammonium hydroxide in methanol (0.53 mL). This solution was then taken to dryness and dissolved in DCM (20 mL) and washed with water (50 mL). The organic fraction was then dried with magnesium sulfate and then taken to dryness to give the pure product as a white solid. Yield: 100%

Compound 39: 1-lsocyanato-4-methoxybenzene (0.50 g, 3.35 mM) and aminomethanesulfonic acid (0.38 g, 3.35 mM) were added to a stirring solution of TBA OH (1N) in methanol (3.35 mL) at room temperature under an inert atmosphere. After 8 hours the mixture was taken to dryness, dissolved in water (10 mL) and washed with DCM (50 mL). The organic phase was dried with magnesium sulfate, taken to dryness giving the crude product as clear oil. The final product was obtained by flash chromatography: ethyl acetate 100% followed by methanol 100%. The methanol fraction was taken to dryness with further addition of TBAOH as necessary to give the pure product as an off white waxy solid. Yield: 33%

Compound 53: Triphosgene (0.309 g; 1.04 mM) was added to a stirring solution of 4-(6-methylbenzo[d]thiazol-2-yl)aniline (0.5 g; 2.08 mM) in ethyl acetate (20 mL) and heated at reflux for 4 hours under nitrogen.

Aminomethanesulfonic acid (0.231 g; 2.08 mM) was added to a stirring solution of tetrabutylammonium hydroxide in methanol (2.08 mL; 2.08 mM) and was then allowed to come to dryness to form a white crystalline solid. This solid was then dissolved in ethyl acetate (5 mL) and added to the refluxing mixture above. This solution was then heated at reflux, under nitrogen overnight, taken to dryness and purified by flash chromatography with 100% ethyl acetate followed by 100% methanol. The methanol fraction was brought to dryness, dissolved in chloroform and washed twice with water. The resulting methanol fraction was then brought to dryness to obtain the final product as a yellow crystalline solid. Yield: 65%

Compound 71: 2-aminobenzothiazole (0.251 g, 1.67 mmol) and CDI (0.268 g, 1.65 mmol) were stirred in DCM (10 ml) at room temperature under an inert atmosphere overnight. The precipitate which formed was removed by filtration. Aminomethanesulfonic acid (0.185 g, 1.66 mmol) was dissolved in 1M tetrabutylammonium hydroxide in methanol (1.66 ml, 1.66 mmol) additional methanol was added to dissolve all reactants, the solution was dried, dissolved in pyridine (2 ml) and added to the precipitate, stirring for 16 hours at room temperature. The mixture was added to water, dried, a smaller volume water was added, the precipitate formed was filtered resulting in a pure product. Yield: 74%

Mode of Action

It has been observed that the compounds of the invention coordinate with the exterior cell surface membranes of bacteria, passing through this barrier and coordinating with cell structures with in the cell. Fluorescent members of this class of compound have allowed us to confirm a strong interaction with the surface of *S. aureus*, a weaker interaction with the surface of *E. coli*, and no detectable interaction with the surface of mammalian cells in culture (e.g. HEK, HELA or CHO cells).

FIG. 1 shows a fluorescence microscopy image of *Staphylococcus aureus* upon the addition of compound 53. The compound is shown in green. We can see the green compound associating with the surface of the cells.

FIG. 2 again shows that through comparison of the fluorescent images on the right and left of the light microscope image in the centre the 53 adheres to surface of both types of bacterial cell (*Staphylococcus aureus* and *E. coli*) but also localises within the *Staphylococcus* cells.

As can be seen from FIG. 3, fluorescence titration experiments with compound 52 also show a change in the UV-Vis spectrum obtained for a sample containing bacteria and compound compared to a spectra containing 52 only. This is indicative of a change in compound environment due to interaction with the cell.

We hypothesise that the compounds interact with lipid surface of cells, the phospholipid composition of which differs between prokaryotes and eukaryotes, giving this class of compounds their selectivity. Once the compounds have coordinated with the lipid membrane in high enough concentration they pass through the cells outer membrane, via the formation of self-associated superstructures, and interact with DNA. As bacteria are unlikely to change their lipid composition, the acquisition of resistance strategies is Unlikely.

Antibacterial Data

The results of the screening tests are given in Table 2. The compounds were screened initially by drop testing methods and then by growth rate methods as it was identified that drop testing methods could give false negatives.

TABLE 2

| Compound | drop test activity | | Grow Rates activity | | | |
| | S. aureus | E. coli | S. aureus Log | S. aureus | E. coli | E. coli Stat |
| --- | --- | --- | --- | --- | --- | --- |
| 1 | Y | N | Y | Y | Y | |
| 2 | Y | N | Y | | Y | |
| 3 | N | N | N/A | N/A | N/A | N/A |
| 4 | Y | N | | | | |
| 5 | N | N | | | | |
| 6 | Y | N | | | | |
| 17 (comp.) | N/A | N/A | N/A | N/A | N/A | N/A |
| 18 | N/A | N/A | N/A | N/A | N/A | N/A |
| 19 | N/A | N/A | N/A | N/A | N/A | N/A |
| 20 (comp.) | N/A | N/A | N/A | N/A | N/A | N/A |
| 21 | N/A | N/A | N/A | N/A | N/A | N/A |
| 22 | N/A | N/A | N/A | N/A | N/A | N/A |
| 31 | Y | N | Y | | | |
| 32 | Y | N | Y | | | |
| 33 | Y | N | Y | | | |
| 34 | Y | N | Y | | Y | |
| 36 | N/A | N/A | N/A | N/A | N/A | N/A |
| 37 | Y | N | Y | | | |
| 38 | Y | N | Y | | Y | |
| 39 | N | N | | | | |
| 40 | N | N | | | | |
| 41 | Y | N | | | | |
| 42 | N | N | | | | |
| 43 | Y | N | Y | | Y | |
| 44 | Y | N | | | | |
| 45 | N | N | N/A | N/A | N/A | N/A |
| 46 (comp.) | N | N | | | | |
| 47 (comp.) | N | N | | | | |
| 48 (comp.) | N | N | | | | |
| 49 (comp.) | N | N | | | | |
| 50 (comp.) | N | N | | | | |
| 51 (comp.) | N | N | | | | |
| 52 | N | N | Y | | Y | |
| 53 | Y | N | Y | | Y | |
| 54 | N | N | | | | |
| 55 | N | N | Y | | | |
| 56 | N | N | Y | | | |
| 61 | N | N | Y | | | |
| 62 | N | N | Y | | | |
| 63 | N | N | | | | |
| 65 | N | N | | | | |
| 68 | Y | N | Y | | | |
| 69 (comp.) | Y | N | Y | | | |
| 71 | N | N | Y | N | | |
| 72 | N | N | N | Y | | |
| 74 | N | N | Y | | | |

Screening Tests (Y = antibacterial activity;
N = No antibacterial activity;
N/A = could not be tested because of solubility issues;
blank = yet to be tested;
log = log phase bacterial growth;
stat = stationary phase growth).

The structures of the comparative compounds are given in Table 3:

TABLE 3

Structures of comparative compounds

17

20

46

TABLE 3-continued

Structures of comparative compounds

47

48

49

50

51

69

TABLE 4

Calculated MIC$_{50}$ and MIC$_{100}$ values.

| | MIC50 (µg/mL) | | | | MIC100 (µg/mL) | | | |
|---|---|---|---|---|---|---|---|---|
| Compound | Staph Log | Staph Stat | Coli Log | Coli Stat | Staph Log | Staph Stat | Coli Log | Coli Stat |
| 1 | 7.35 | 209.132 | | 412.0789 | 29.41365 | 254.5639 | | 421.0559 |
| 2 | 54.13 | | | | 93.55125 | | | |
| 31 | 21.6 | 14.78909 | | | 22.68037 | 14.83815 | | |
| 32 | 19.14 | 39.39941 | | | 20.08159 | 56.99733 | | |
| 33 | 0.45 | 5.578963 | | | 2.97104 | 7.303807 | | |
| 34 | 146.6192 | | | | | | | |
| 37 | 29.08 | 464.1399 | 236.9979 | 450.9874 | 30.34688 | 559.1301 | 505.6726 | 480.2477 |
| 52 | 330.0044 | | | | | | | |
| 53 | 21.10713 | | | | | | | |
| 68 | 370.0761 | | | | | | | |

The results show a correlation between the presence of the aromatic unit 'Ar' in the compounds of formula (I) and antimicrobial activity. For example, compounds 46-51, which all possess aliphatic chains instead of the Ar group, show no activity in the tests. It is also thought that the oxygen-containing anionic unit plays an important role. Comparative data with compounds of formula (I) with non-anionic 'A' groups is difficult, however, as such compounds have poor solubility and thus their antimicrobial activity cannot readily be established.

The invention claimed is:

1. A method of reducing the number or preventing the multiplication of live Gram-negative and/or Gram-positive bacteria on a surface comprising a step of applying to the surface a solution of a compound of formula (I):

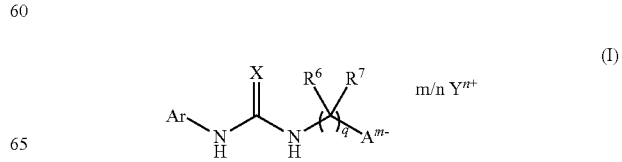
(I)

wherein
Ar is

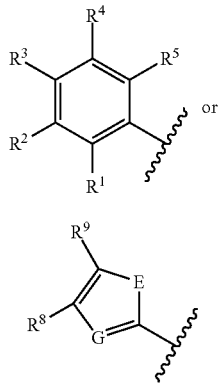
(Ar1)

(Ar2)

X is O, S, or NH;
A is such that $A^{m-}$ is an oxygen-containing anionic group;
Y is such that $Y^{n+}$ is an inorganic or organic cation or proton (Ft);
G is N or CH;
E is S, O or NH;
$R^6$ and $R^7$ are independently selected for each value of q from hydrogen or a straight-chain, branched chain or cyclic or polycyclic $C_1$ to $C_{10}$ hydrocarbyl group;
$R^1$-$R^5$, $R^8$ and $R^9$ are selected from hydrogen, —$CF_3$, —$CCl_3$, —$NHR^{10}$, —$NR_2^{10}$, —$OR^{10}$, —OH, —NHC(O)$R^{10}$, —OCOR$^{10}$, —COH, —COR$^{10}$, COOH, COOR$^{10}$, CONH$_2$, —CN, —SO$_3$H NO$_2$, —OMe, —NH$_2$, halogen, CONHR$^{10}$, —C(O)NH(CH$_2$)SO$_3$—, a straight-chain, branched chain or cyclic or polycyclic $C_1$ to $C_{10}$ hydrocarbyl group, a cyclic or polycyclic group comprising 1 or more heteroatoms selected from O, N and S and optionally further substituted with a straight-chain or branched chain C1-C8 hydrocarbyl group, or a nucleobase-containing group

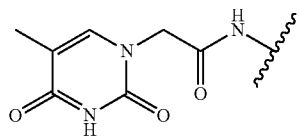

wherein, optionally, at least one of the pairs of groups $R^1$/$R^2$, $R^2$/$R^3$, $R^3$/$R^4$ and $R^4$/$R^5$ is such that the pair(s) form a cyclic or polycyclic moiety, optionally comprising one or more heterotatoms, fused to the benzene ring in Ar1, or the pair $R^8$/$R^9$ forms a cyclic or polycyclic moiety fused to the ring substituted with G and E in Ar2 wherein the cyclic or polycyclic moiety is optionally substituted with a straight-chain or branched chain C1-C8 hydrocarbyl group;
$R^{10}$ is a straight-chain, branched chain or cyclic or polycyclic $C_1$ to $C_{10}$ hydrocarbyl group;
q is an integer from 1-10; and
m and n are each independently an integer from 1-3.

2. The method of claim 1, wherein $A^{m-}$ is selected from —SO$_3^-$, —PO$_3$H$^-$, PO$_3^{2-}$, or —COO$^-$.

3. The method of claim 1, wherein Y is selected from pyridinium, tetraalkylammonium, alkali metal, or alkaline earth metal.

4. The method of claim 1, wherein G is N and E is S.

5. The method of claim 1, wherein
if Ar=Ar1, at least one of $R^1$-$R^5$ is selected from CF$_3$, NO$_2$, OMe, NMe$_2$, NH$_2$, F or from the following groups:

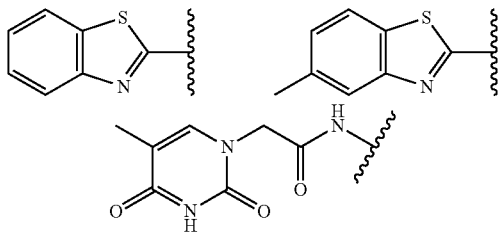

and/or at least one of the pairs of groups R1/R2, R2/R3, R3/R4 and R4/R5 form a cyclic or polycyclic moiety, optionally comprising one or more heterotatoms; or
if Ar=Ar2, R1 and R2 form a benzene ring fused to the ring substituted with G and E, wherein the benzene ring is optionally substituted with a straight-chain or branched chain C1-C8 hydrocarbyl group.

6. The method of claim 1, wherein said Gram-positive bacteria are staphylococci, and/or wherein said Gram-negative bacteria are Enterobacteriaceae.

7. A method of treatment of a bacterial infection, comprising administering to an animal an effective amount of a composition comprising at least one compound of formula (I):

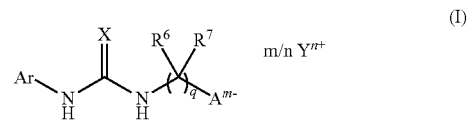
(I)

wherein
Ar is

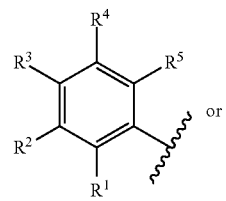
(Ar1)

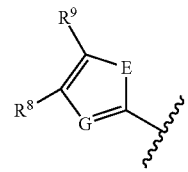
(Ar2)

X is O, S, or NH;
A is such that $A^{m-}$ is an oxygen-containing anionic group;
Y is such that $Y^{n+}$ is an inorganic or organic cation or proton (H$^+$);
G is N or CH;
E is S, O or NH;

$R^6$ and $R^7$ are independently selected for each value of q from hydrogen or a straight-chain, branched chain or cyclic or polycyclic $C_1$ to $C_{10}$ hydrocarbyl group;

$R^1$-$R^5$, $R^8$ and $R^9$ are selected from hydrogen, —$CF_3$, —$CCl_3$, —$NHR^{10}$, —$NR_2^{10}$, —$OR^{10}$, —OH, —NHC(O)$R^{10}$, —$OCOR^{10}$, —COH, —$COR^{10}$, COOH, $COOR^{10}$, $CONH_2$, —CN, —$SO_3H$ $NO_2$, —OMe, —$NH_2$, halogen, $CONHR^{10}$, —C(O)NH(CH$_2$)SO$_3$—, a straight-chain, branched chain or cyclic or polycyclic $C_1$ to $C_{10}$ hydrocarbyl group, a cyclic or polycyclic group comprising 1 or more heteroatoms selected from O, N and S and optionally further substituted with a straight-chain or branched chain C1-C8 hydrocarbyl group, or a nucleobase-containing group

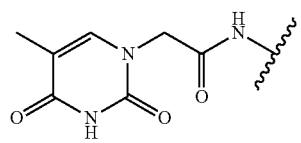

wherein, optionally, at least one of the pairs of groups $R^1/R^2$, $R^2/R^3$, $R^3/R^4$ and $R^4/R^5$ is such that the pair(s) form a cyclic or polycyclic moiety, optionally comprising one or more heterotatoms, fused to the benzene ring in Ar1, or the pair $R^8/R^9$ forms a cyclic or polycyclic moiety fused to the ring substituted with G and E in Ar2 wherein the cyclic or polycyclic moiety is optionally substituted with a straight-chain or branched chain C1-C8 hydrocarbyl group;

$R^{10}$ is a straight-chain, branched chain or cyclic or polycyclic $C_1$ to $C_{10}$ hydrocarbyl group;

q is an integer from 1-10; and m and n are each independently an integer from 1-3.

8. The method as claimed in 7, wherein the Gram-positive bacteria are staphylococci, and/or the Gram-negative bacteria are Enterobacteriaceae.

9. The method of claim 7, wherein the composition further comprises at least one antibiotic compound selected from the group consisting of a beta-lactam antibiotic, a macrolide antibiotic, a cephalosporin antibiotic, a fluoroquinolone antibiotic, a sulfonamide antibiotic, a tetracycline antibiotic, an minoglycoside antibiotic, and combinations thereof.

10. The method of claim 1, wherein $R^6$ and $R^7$ are each hydrogen.

11. The method of claim 1, wherein q is an integer from 1 to 6.

12. The method of claim 11, wherein q is an integer from 1 to 4.

13. The method of claim 1, wherein m and n are each 1.

14. The method of claim 3, wherein Y is selected from the group consisting of pyridinium, TBA (N″Bu$_4$), TPA (N″Pr$_4$), TEA (N″Et$_4$), TMA (N″Me$_4$), THA (N″Hex$_4$), Na, K and TPeA (N″Pe$_4$).

15. The method of claim 7, wherein the animal is a mammal.

16. The method of claim 15, wherein the mammal is a human.

17. The method of claim 1, wherein the compound of formula (I) is selected from one of the following compounds:

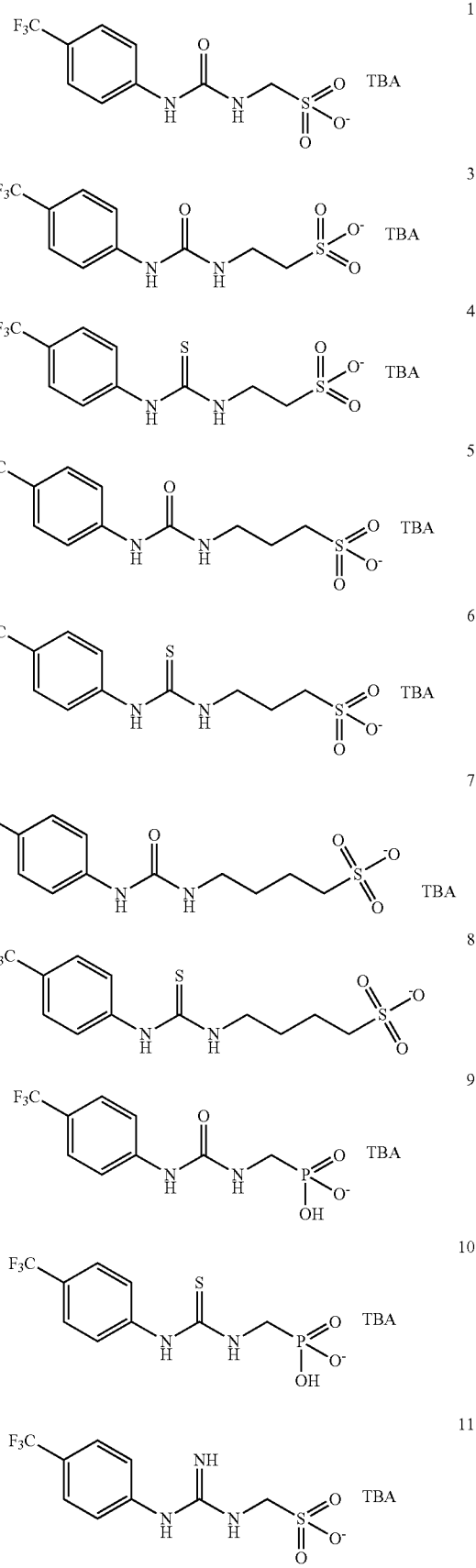

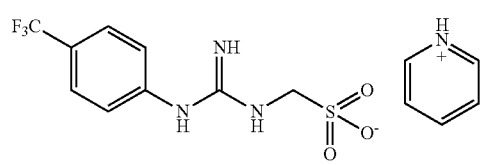 12
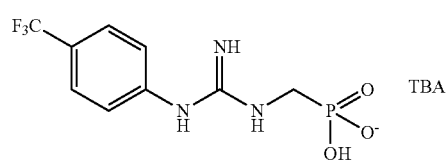 13 TBA
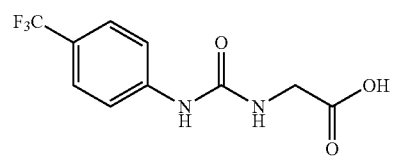 18
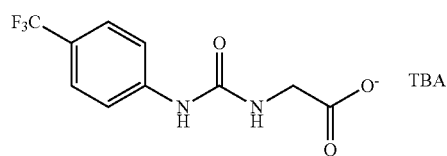 19 TBA
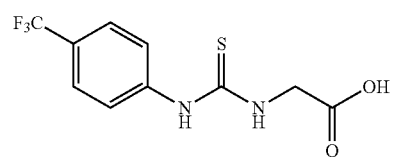 21
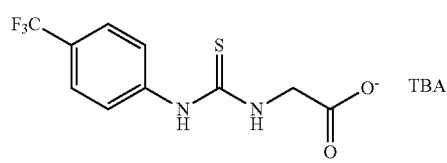 22 TBA
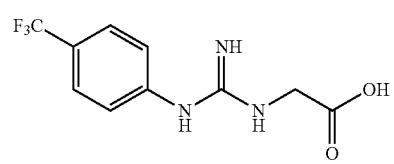 25
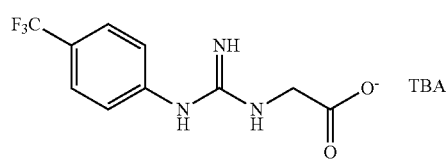 26 TBA
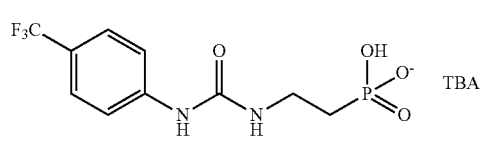 27 TBA
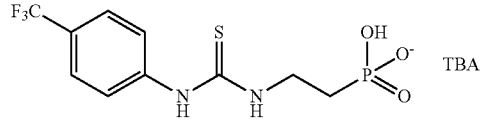 28 TBA
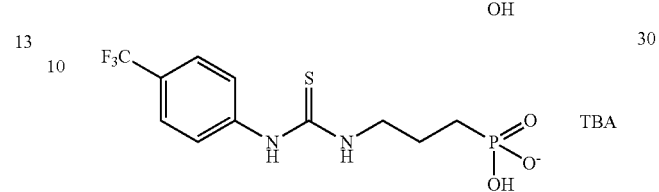 29 TBA
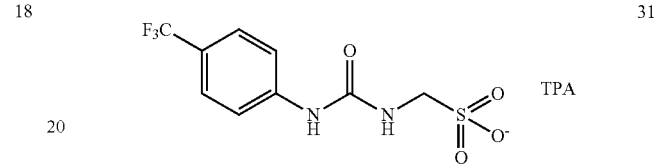 30 TBA
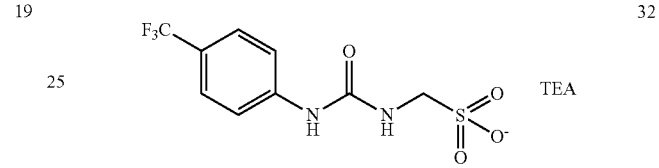 31 TPA
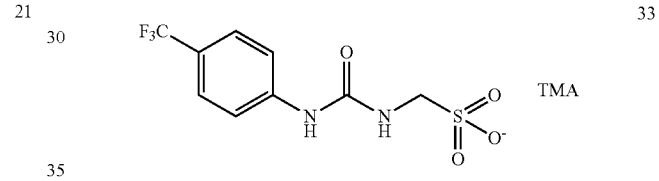 32 TEA
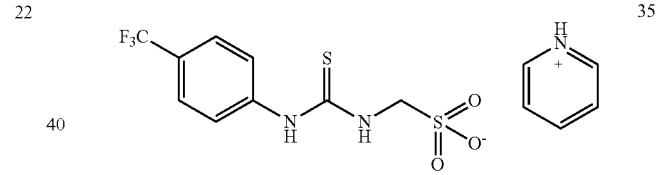 33 TMA
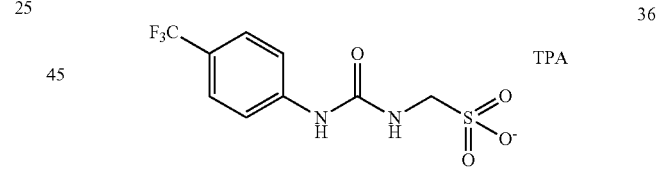 35
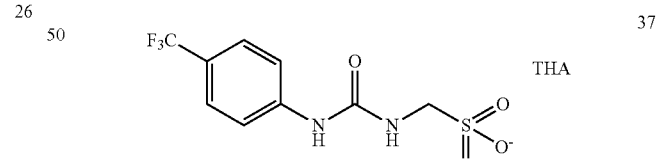 36 TPA
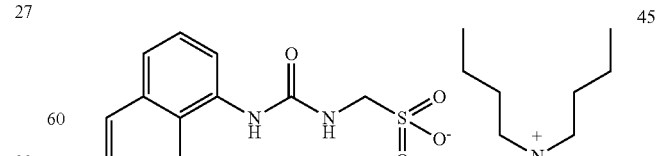 37 THA
 45

-continued
52
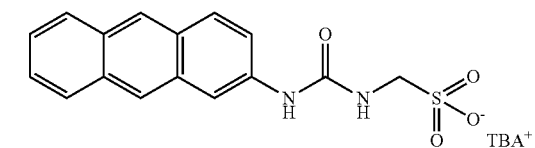
TBA⁺
53
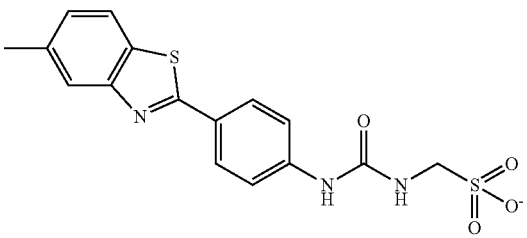
TBA⁺
54
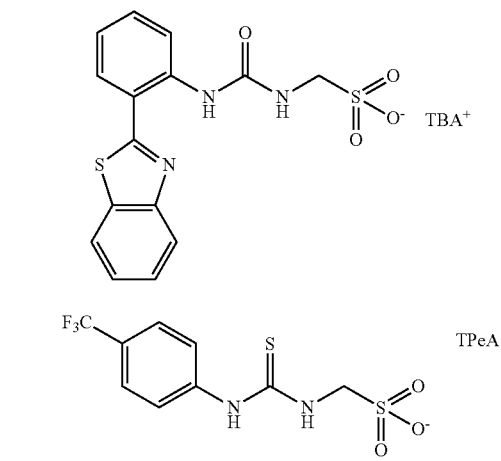
TBA⁺
57
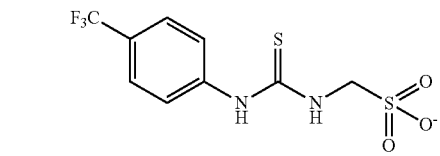
TPeA
58
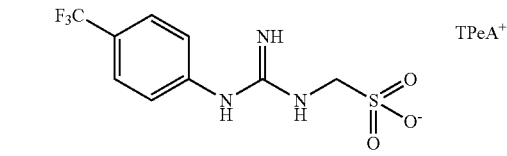
Na⁺
59
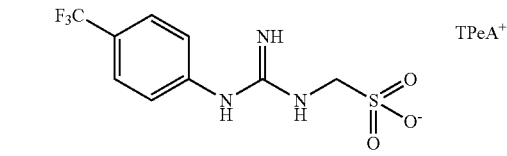
K⁺
60
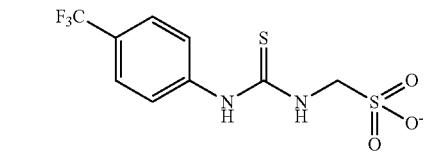
TPeA⁺
61
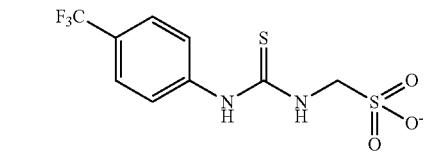
TMA⁺
-continued
62
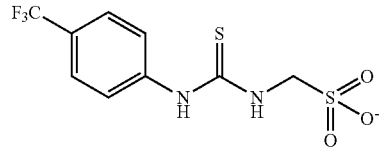
TEA⁺
63
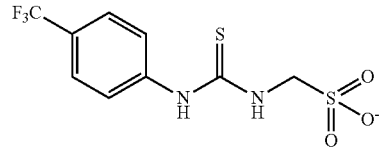
TPA⁺
64
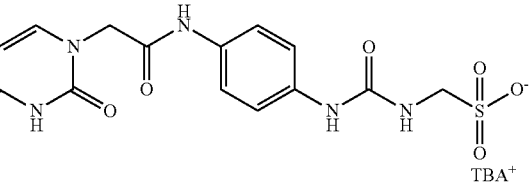
TBA⁺
65
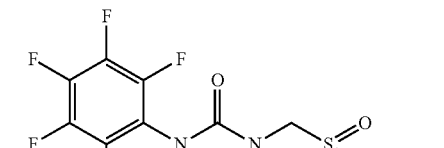
TBA⁺
66
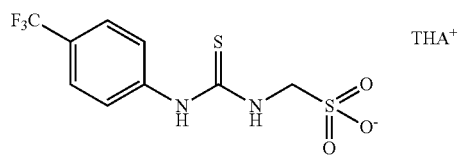
THA⁺
67
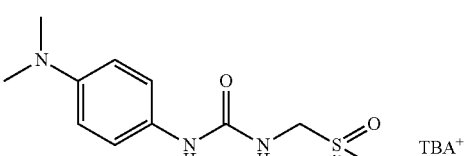
TBA⁺
71
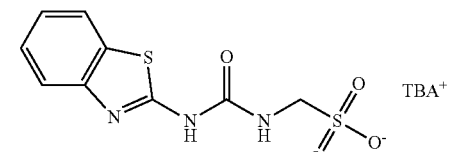
TBA⁺
72
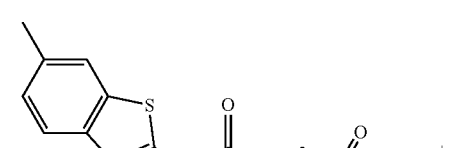
TBA⁺
73
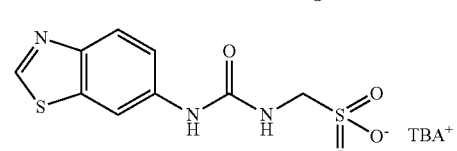
TBA⁺

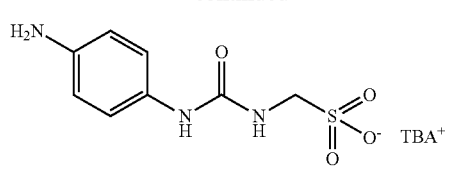
74
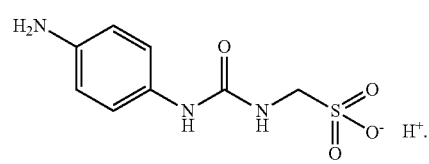
75
18. The method of claim 17, wherein the compound of formula (I) is:
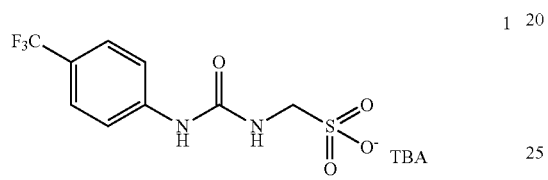
1